United States Patent [19]
Horn

[11] Patent Number: 6,039,924
[45] Date of Patent: Mar. 21, 2000

[54] CHEMICAL SAMPLE TREATMENT SYSTEM AND CASSETTE, AND METHODS FOR EFFECTING MULTISTEP TREATMENT PROCESS

[75] Inventor: Marcus J. Horn, Redwood Shores, Calif.

[73] Assignee: Amersham Pharmacia Biotech AB, Uppsala, Sweden

[21] Appl. No.: 09/146,160

[22] Filed: Sep. 3, 1998

Related U.S. Application Data

[60] Continuation of application No. 08/802,511, Feb. 20, 1997, Pat. No. 5,918,273, which is a division of application No. 08/679,355, Jul. 9, 1996, Pat. No. 5,800,784.

[51] Int. Cl.[7] .................................................. G01N 35/10
[52] U.S. Cl. ............................................................ 422/67
[58] Field of Search .................................. 422/67, 63, 70, 422/101, 102; 436/54; 141/130; 73/61.55

[56] References Cited

U.S. PATENT DOCUMENTS

| | | | |
|---|---|---|---|
| 3,518,164 | 6/1970 | Andelin et al. | 422/99 |
| 3,559,454 | 2/1971 | Evans | 73/864.82 |
| 3,996,017 | 12/1976 | Kaiser | 73/23.35 X |
| 4,046,634 | 9/1977 | Mercer | 435/16 |
| 4,096,825 | 6/1978 | Golias et al. | 73/61.55 X |
| 4,102,179 | 7/1978 | Snell | 73/61.56 |
| 4,166,720 | 9/1979 | Weber | 73/866 X |
| 4,186,607 | 2/1980 | Porter et al. | 73/61.55 |
| 4,285,698 | 8/1981 | Otto et al. . | |
| 4,376,391 | 3/1983 | Brunnee . | |

(List continued on next page.)

FOREIGN PATENT DOCUMENTS 155360  9/1983  Japan .

OTHER PUBLICATIONS

*Patent Abstracts of Japan* Grp P819, vol. 13, No. 37, Abs pub date Jan. 27, 1989 (63–235858) "Selection of LC Eluting Conditions and Minicolumn" Ishida et al.

Nugent, K.D.; Burton, W.G.; Slattery, T.K.; Johnson, B.F.; Snyder, L.R. Jun. 29, 1988, J. Chrom. 443, 381–397.

Hewlett–Packard Product Brochure: The HP G1004A Protein Chemistry Station minimizes sample handling and sample loss in HPLC and sequencing analysis. (23) 5091–5168E Nov, 1992) (4 pp.).

Hewlett–Packard Product Brochure: Increase lab productivity with the HP G005A Protein Sequencing System. (23–5091 5170E Nov. 1992) (7 pp.).

*Primary Examiner*—Thomas P. Noland
*Attorney, Agent, or Firm*—Sabath & Truong; Robert P. Sabath; Stanley N. Progital

[57] ABSTRACT

This invention is directed to a cassette chemical immobilization and treatment system and method for enabling the performance of various complex chemistries with minimal human intervention, near-zero dead volume, and flow-through protocols pursuant to a predetermined instruction set encoded on a multiple-address chemical treatment cassette assembly. The cassette assembly having a high-pressure interface capability to permit direct insertion of the mini-column into a high-pressure solvent line for use as a support column for HPLC analysis. A sample loader loads analyte samples either singly or simultaneously into the multiple, addressable mini-columns without the need to load the sample funnel/column assembly into a separate reaction chamber. The invention system reads the machine readable instruction code and performs chemistries on the analyte, including mixing solvents, reactants and buffers; detaching and shuttling the analyte back and forth performing complex chemistries either on or off-column; solvation of powdered or lyophillized reagents; and performing in-line, on-board analysis. These protocols are performed automatically pursuant to instructions contained on a bar code, without having to remove the cassette or interface from the CTS or otherwise require human intervention. The same chemistries may be performed on all sample mini-column addresses, or a separate completely independent set of protocols may be defined for each address, or for each block of addresses pursuant to the instructions contained in the machine readable code on the cassette.

10 Claims, 14 Drawing Sheets

U.S. PATENT DOCUMENTS

| | | | |
|---|---|---|---|
| 4,692,308 | 9/1987 | Riley et al. | 422/65 |
| 4,915,847 | 4/1990 | Dillon et al. | 422/101 X |
| 4,929,426 | 5/1990 | Bodai et al. | 422/63 |
| 4,932,081 | 6/1990 | Burns | 422/102 |
| 5,045,196 | 9/1991 | Fang | 422/101 X |
| 5,084,242 | 1/1992 | Sakuma et al. | |
| 5,178,832 | 1/1993 | Phillips et al. | 422/60 |
| 5,228,988 | 7/1993 | Sanford et al. | |
| 5,229,074 | 7/1993 | Heath et al. | 422/67 X |
| 5,236,666 | 8/1993 | Hulette et al. | 422/67 X |
| 5,358,641 | 10/1994 | Sanford et al. | 422/70 X |
| 5,374,395 | 12/1994 | Robinson et al. | 422/63 X |
| 5,439,645 | 8/1995 | Saralegui et al. | 422/67 X |
| 5,468,643 | 11/1995 | Su et al. | |
| 5,500,071 | 3/1996 | Kaltenbach et al. | 73/61.52 |
| 5,529,899 | 6/1996 | Wheelock et al. | 435/6 |
| 5,571,410 | 11/1996 | Swedberg et al. | 422/70 |
| 5,578,268 | 11/1996 | Champseix et al. | 422/63 |
| 5,580,528 | 12/1996 | Demers | 422/102 X |
| 5,589,063 | 12/1996 | Sanford et al. | 73/61.55 X |
| 5,602,037 | 2/1997 | Ostgaard et al. | 422/101 X |
| 5,645,702 | 7/1997 | Witt et al. | 204/501 |
| 5,646,046 | 7/1997 | Fischer et al. | |
| 5,658,413 | 8/1997 | Kaltenbach et al. | 422/70 |
| 5,697,409 | 12/1997 | Bishop et al. | 141/130 X |
| 5,762,873 | 6/1998 | Fanning et al. | 422/65 X |
| 5,800,784 | 9/1998 | Horn | 422/101 |
| 5,814,277 | 9/1998 | Bell et al. | |
| 5,885,530 | 3/1999 | Babson et al. | 422/67 |

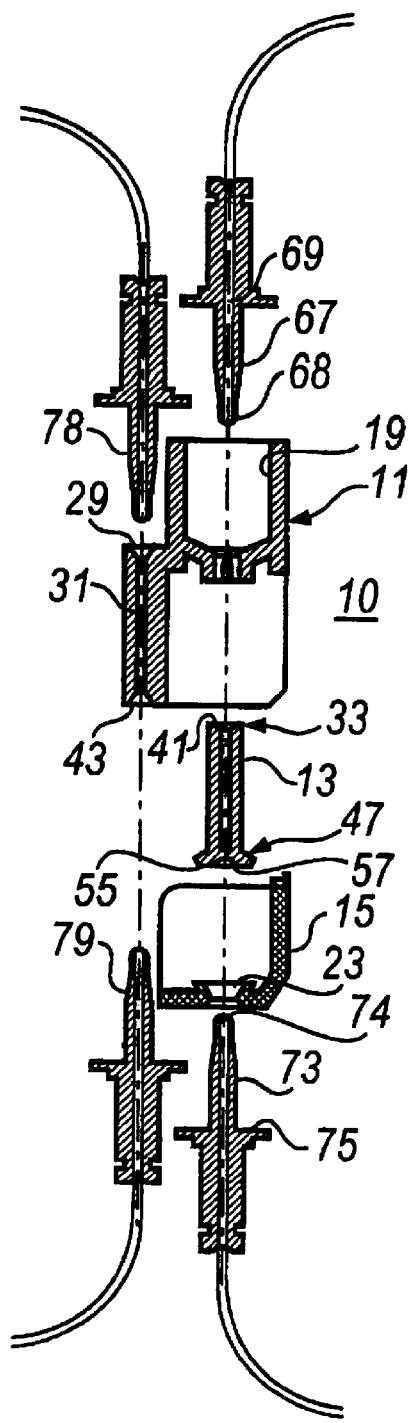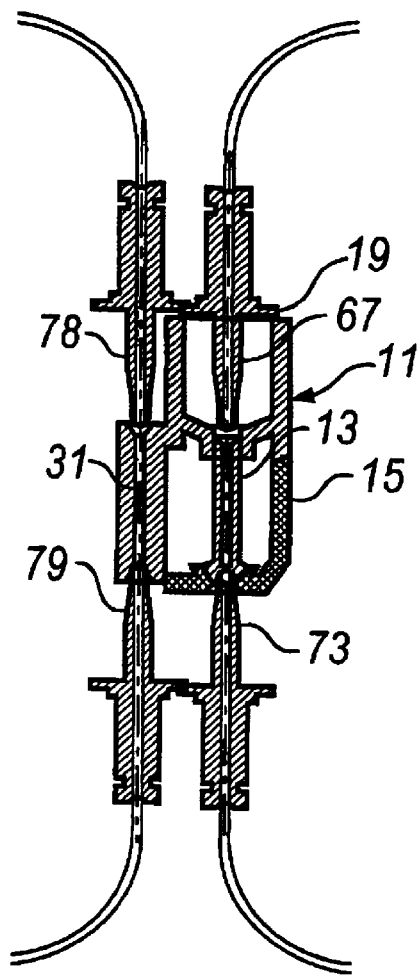
FIG. 5A
FIG. 5B

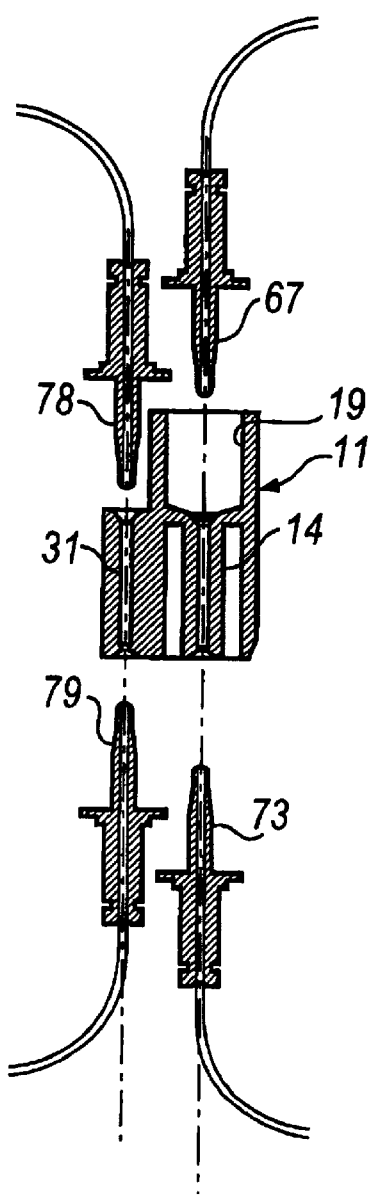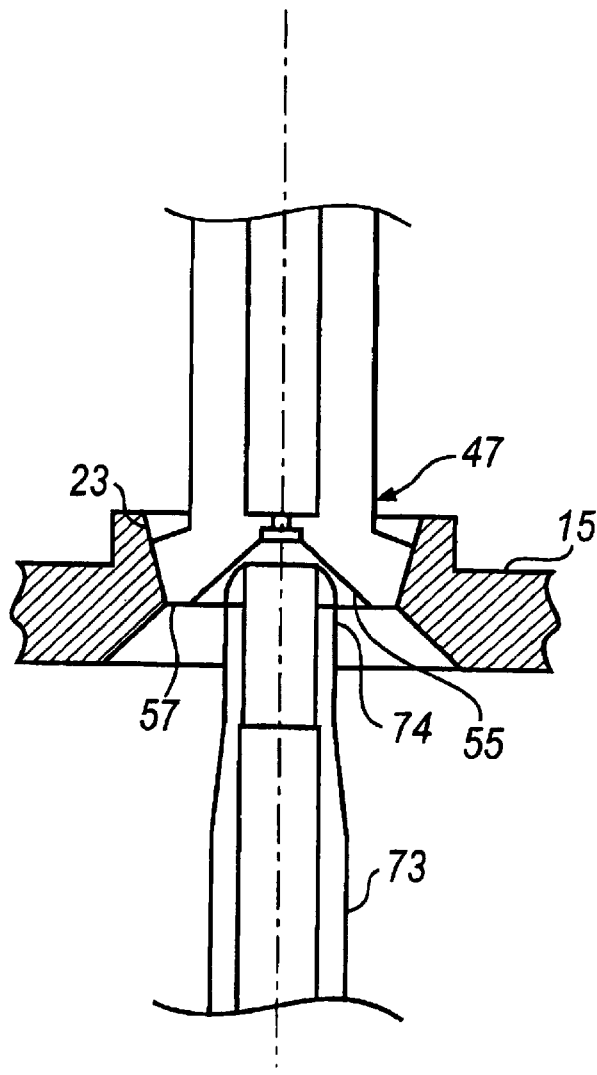
FIG. 6
FIG. 7

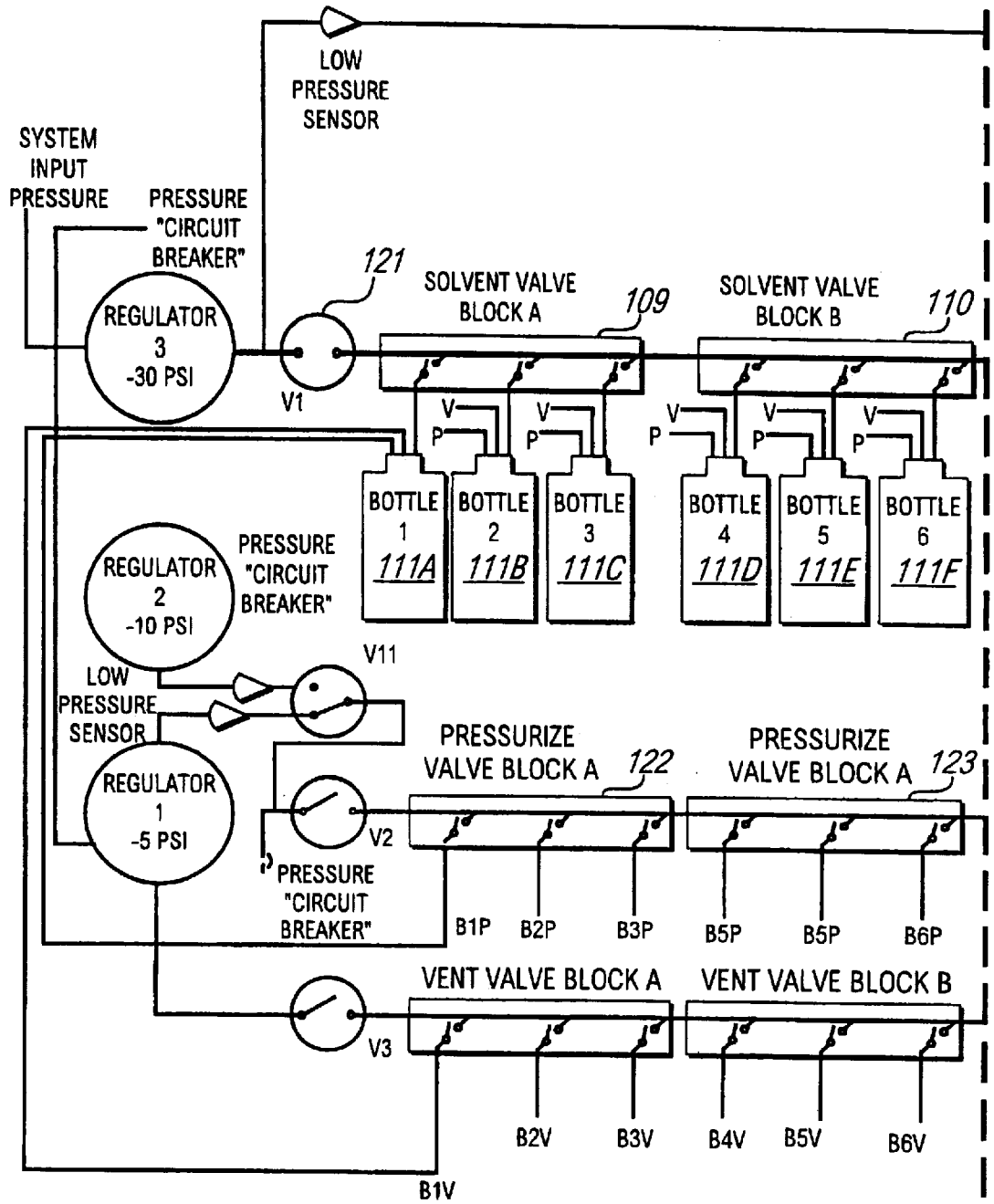
FIG. 10A
KEY TO FIG. 10
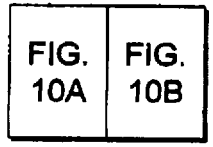

CHEMICAL SAMPLE TREATMENT SYSTEM AND CASSETTE, AND METHODS FOR EFFECTING MULTISTEP TREATMENT PROCESS

This is a Continuation of application Ser. No. 08/802,511 filed on Feb. 20, 1997 and now U.S. Pat. No. 5,918,273, which is a division of application Ser. No. 08/679,355, filed Jul. 9, 1996, and now U.S. Pat. No. 5,800,784.

BACKGROUND OF THE INVENTION

1. Technical Field

The present invention relates to a cassette-type chemical sample treatment system apparatus and method for use in the treatment of less than one milligram quantities of amino acids, proteins, peptides, and the like pursuant to predetermined or preselected chemical, biochemical, and biomedical protocols. More particularly, the invention of this application relates to a cassette-type chemical sample treatment system and method having a cassette for holding a plurality of sample columns for immobilizing preselected samples and a plurality of reagent wells for retaining preselected reagents for enabling predetermined chemistries of the preselected samples with the preselected reagents, including column loading, treatment, and post-treatment analysis of the reacted sample with near-zero dead volume and minimal human intervention, the predetermined chemistries being specified by machine readable code integrated into the cassette.

2. Background Art

With the exception of certain high-performance liquid chromatography (HPLC), proteins and peptides are typically fractionated in aqueous buffers containing amines, salts and, often, denaturants. Therefore, additional manipulations such as desalting by HPLC, precipitation, or dialysis are required to render the sample matrix compatible with protein and peptide chemistry or peptide sequencing protocol. Each of these additional steps, however, involves potential losses, especially when only less than milligram amounts of protein are present at low concentrations. It is generally understood that proteins include peptides, accordingly, for purposes of this invention, no distinction is made between peptides and proteins, and reference to one will also apply to the other.

Many of the steps involved with the aforementioned steps have been eliminated by immobilizing a protein or a peptide directly onto a solid support, washing away any interfering components, and leaving the protein bound to the support ready for either further on-column chemistries or removed for analysis. Hewlett-Packard Analytical Instruments (Palo Alto, Calif., US) manufactures a family of analytical devices (HP-G1000A, HP-G1004B, and HP-G1005A) which use sample columns containing a solid support upon which proteins or peptides might be immobilized. The HP-G1004A is a Protein Chemistry Station (PCS) which permits on-column chemistries to proteins and peptides immobilized on a hydrophobic support. The HP-G1005 performs standard Edman degradation protocols on a peptide immobilized on a bi-phasic support for the performance of peptide sequencing.

Post-translational modifications will determine the stereochemistry and conformation of the peptide. Accordingly, there is a need to determine the nature of the side groups so that a conformational analysis or a structure determination may be made. Such post-translational modification chemistries may be carried out manually or semi-automatically whereby a sample is subjected to reaction with the appropriate reagents to give an appropriate indication in the event the post-translational modification is present. The HP-G004 Protein Chemistry Station (PCS) represents the state of the art with respect to enabling semi-automatic performance of chemistries. The PCS has limitations, however, with respect to the types and complexity of chemistries that might be performed on this system. For example, the PCS is not able to perform bi-directional pumping; it can only pump down. This limitation precludes shuttling sample or reagents back and forth through the support. This feature would be desirable, for example, when the reactivity of a side group is affected by the polarity of a solvent and the appropriate solvent is one that may separate tie sample from the support. Second, the chemistries performed in the PCS require that the reagents be dispensed into a large funnel in order to be introduced to the reaction. Without changing-out the funnel between reagents, a significant risk of cross-contamination is created.

The HP PCS system employs a hydrophobic column to immobilize the sample during loading and during application of the chemistry. FIG. 1 is a cross-sectional diagram of single sample reaction chamber typical of the background art. A funnel a is press-fit attached to the inlet side of the hydrophobic column b, with the throat of the funnel c in communication with the top opening of the column d. The funnel/column assembly is loaded into a center cavity e of a clear Lucite reaction chamber f, the assembly being secured by compressing and twisting the funnel/column assembly in a single movement into a bayonet-type connection on the walls of the Lucite holder g, and the column being urged against the funnel by a spring k. A cap h is screwed onto the reaction chamber so as to seal the system. Inlet ports i,j in the cap permit the introduction of sample into the funnel and the introduction of a pressurized inert gas to pump the reagent through the column. During the chemistries performed on the PCS, the funnel is never changed-out. As a result, a serious concern with the system and method of the background art is that the side walls of the funnel may retain residues of previously introduced reagents, thus resulting in cross-contamination or reagents.

After insertion and bayonet-locking of the funnel/column assembly into the reaction chamber, a protein or peptide solution sample is loaded in the 5 ml funnel attached to the column. The cap is screwed onto the holder and over the funnel so that pressurized nitrogen, or other inert gas, may be applied to the sample and pressure forced into and through the hydrophobic sample column. The sample loading process captures proteins and peptides on the hydrophobic portion of the sample column, while the sample solvent passes through.

It is possible to do multiple sample additions for larger volumes or to use a second solution to wash the sample. First, the holder cap removed, and a second sample or aqueous wash is added to the funnel, the cap reattached to the holder, and the holder pressurized with nitrogen, thus forcing the aqueous wash through the hydrophobic sample column.

Following the sample loading, sample preparation (rinses), and possible sample pre-treatment, the funnel/column assembly is removed from the sample reaction chamber and is transferred to another reaction chamber in the Protein Chemistry Station, wherein the appropriate reagents are administered to perform the desired chemistries. A technician selects a computer program which directs the PCS, via a micro-controller interface, to dispense the appropriate reagent into the sample funnel pursuant to the selected program. The appropriate reagent is directed through a tube and into a reagent port in the cap of the reaction chamber. The reagent flows from the reagent port into the sample funnel. Pressurized inert gas then forces the reagent out of the sample funnel and into the column.

All chemistries are carried out in the column or the funnel, and within the reaction clamber. Also, since only one reaction chamber may be loaded at a time in the PCS, preparation and treatment of multiple sample columns is a time consuming and tedious effort. Further, the PCS provides only four reservoirs for reagents, buffers or solvents, all of which must be a liquid. Additionally, there may be reactions, especially of biomedical interest, wherein a solid reagent, such as a lyophilized enzyme, vaccine, hormone preparations, and the like which exhibit lower stability in solution, tending to either degrade rapidly or require low storage temperatures in its hydrated state, may be needed in order to execute the desired chemistry. The devices of the background art are not able to accommodate these dry reagents. Accordingly, there is a need for an automated chemical treatment system capable of performing a multiplicity of both peptide and post-translational modification chemistries sequentially on a plurality of samples, in an uninterrupted manner with minimal human intervention or direction. The automated chemical treatment system would also provide means to perform chemistries external to the sample columns and for reintroduction of the reacted sample or analyte to the sample column. Also, there is a need for an automated system that would provide means for "just-in-time" delivery of reagents requiring just-in-time solubilization, such as adsorbed, lyophilized or other powdered reactants to the sample.

Since the same sample funnel is used for all reagents there is a risk of cross-contamination that may affect the outcome of sensitive chemistries. Minute quantities of reagent may adhere to the walls of the funnel, only to be eluted into the sample column when the next reagent is introduced into the funnel. Where less than one milligram quantities of peptides or proteins are being investigated, the presence of minute amounts of impurities or cross-contaminants may have a significant impact on the results. Accordingly, there is a need for a sample column/reaction chamber system that permits near-zero dead volume to minimize risk of cross contamination and the resulting inaccuracies such contamination may cause.

Once the protein chemistries are complete, the sample column from the PCS is removed from the sample reaction chamber and is transferred to the appropriate analytical measurement device in order to measure or characterize the results of the chemistries performed. Typically, the analysis is selected to characterize the products of a peptide cleavage.

Typically, RP-HPLC is used to analyze the reaction products. Ideally, it would be desirable to insert the sample column of background art directly into an HPLC sample column holder, thus integrating the sample column into the HPLC and transforming the sample column into a RP-HPLC column. In order to obtain adequate separation of proteins, however, column pressures greater than 1500 psi are required. The sample column of the background art rated to withstand pressures up to approximately 1000 psi. At pressures greater than 1000 psi, the non-tapered end of the sample column typically fails. In order to operate at the extremely high pressures required for protein separation, a special adapter is required, and is attached to the inlet end of the sample column to accommodate a high pressure line fitting. FIG. 2 shows a cross-section diagram of the sample column and adapter typical of the background art. The adapter 1 is inserted into the non-tapered end d of the sample column b. Since the sample column is a pre-column to the chromatography column of the HPLC, the adapter is also a part of the HPLC pre-column. Accordingly, the column plus adapter of the background art is supplied in addition to the standard chromatogragh column rather than as a substitute column. Consequently, the adapter 1 must also be packed with a hydrophobic support m, and once it is affixed to the outlet end d of the hydrophobic column, becomes an extension of the original hydrophobic column upon which the sample is immobilized. As a result, the adapter may be used only once and then must be discarded. Accordingly, there is a need for a sample column able to withstand the high pressures of RP-HPLC that might be directly incorporated, without an adapter or modification, into an HPLC receptacle so as to integrate the sample column as the chromatography column of the RP-HPLC.

The above single-sample procedures associated with the current state of the art device are incapable of performing chemistries or sequential, uninterrupted treatment of multiple samples and results, therefore, in extremely tedious protocols and prone to cross-contamination. Further, a well recognized problem associated with the incorporation of the hydrophobic column into the RP-HPLC is that the coupling between the inlet port of the column and the RP-HPLC line is such that residual liquids are trapped in the headspace between the end of the column support material and the RP-HPLC coupling. It is well known in the art that a zero-head space is required in order to assure the most accurate HPLC measurements. The existence of a non-zero head space introduces errors into the HPLC analysis.

Chemical procedures and treatments performed on a sample in preparation for analysis can become tedious, particularly where repetitive chemistries must be performed and time consuming where hundreds or thousands of samples are involved. Additionally, it also creates significant opportunities for errors in measurement, and for contamination of the sample or reagents. Further, if characterization of the sample requires several different chemistries to be performed there is an increased chance of error as the technician must now identify, track, and monitor the progress of each of the required protocols. Although the present state of the art includes micro-controller interface with semi-automated apparatus, the technician must still determine which chemical procedure or protocol is to be performed on any particular sample, and key that protocol selection into the micro-controller. If the technician executes the incorrect protocol, the sample is ruined at best, or, at worst the erroneous analytical data recorded on that sample is included in the data being accumulated.

There is a need to provide an automated means for sequential, uninterrupted performance of chemistries on a plurality of samples contained within or immobilized on a plurality of sample columns with minimal human intervention and reduced risk of performing incorrect protocols.

SUMMARY OF THE INVENTION

This invention is directed to a cassette-type chemical treatment system and method for enabling the performance of various chemistries with minimal human intervention, near-zero dead volume, and flow-through protocols pursuant to a predetermined instruction set encoded on the cassette.

The cassette comprises a plurality of sample columns ("mini-columns"), reagent wells, sample loading funnels, alignment means for the sample columns, and a machine readable instruction code set for determining a chemical treatment protocol. All components are constructed from inert materials including but not limited to linear polyethylene, fluoro-copolymers, Teflon®, and the like.

The mini-columns contain a long inner chamber packed under pressure with a solid support, preferably silica, although other supports such as polymer beads, resins, and cellulose may be used. Alternately, no solid support at all need be used when, for example, the sample is retained as a dry powder or beads, or if the sample is microencapsulated. In the preferred embodiment, a silica support is employed and derivatized to render it hydrophilli or hydrophobic. For protein chemistries, the silica support is derivatized with a lipophilic alkyl group thus rendering the support non-polar. Consequently, lipophilic proteins dissolved or suspended in a more polar mobile phase will become immobilized on the hydrophobic support. Unlike the mini-columns of the prior art, both terminal ends of the mini-columns of this invention are designed to accommodate the extremely high pressures (greater than 1200 psi) needed to perform reverse-phase HPLC of the immobilized proteins or other hydrophobic moieties. This is accomplished by designing a generally concave, preferably tapered opening at each end of the column so that an interface means may be attached thereto with near-zero dead volume. The opening can be spheroidally concave, parabolic, conically tapered, and the like so long as a high pressure seal can be effected with a compression fit interface means. Suitable compression fit interface means include: a nozzle having a rounded tip for insertion and compression fit against the walls of the generally concave, preferably tapered opening; a nozzle having a conical tip for insertion inside the inner diameter of the longitudinal chamber for compression fit against the junction of the inner wall of the longitudinal chamber at apex of the generally concave, tapered opening with the conical nozzle; and the like to permit localized interface wit the inlet and outlet ports to enable near-zero dead volume communication. The term "localized interface" in the context of this invention refers to a near-zero dead volume interface wherein the surface area of the connection does not extend beyond the generally concave, preferably tapered walls of the mini-column opening, thus significantly reducing or minimizing the surface area in which reagents, solvents, and detached samples might contact. This is contrasted to the prior art where introduction of reagents and solvents is by dispensing the reagent or solvent into the same sample funnel resulting in a significant risk of cross-contamination. In the preferred embodiment, the distal end of a rounded nozzle is inserted into the generally concave, preferably tapered opening, seated against the sides of the taper, and urged with sufficient force to provide a pressure tight seal so as to withstand column pressures up to 2000 psi. This feature permits the column of this invention to be directly integrated as the support column in a reverse-phase HPLC apparatus. The outlet end of the mini-column may also contain a generally concave, preferably tapered shoulder to mate with an alignment assembly, described below.

As described above, each mini-column may be loaded with a hydrophobic support. The ends of each column are fitted with a porous frit to permit liquid flow and to retain the solid support within the column chamber. The frit may be made from any inert material such as sintered glass, fluorinated polymers, and other polymers such as sintered polypropylene.

A novel feature of the cassette of this invention is that it includes a plurality of loading funnels to provide a funnel assembly. The funnels may be arranged in whatever configuration is deemed expedient in view of the ability of the treatment station to address each mini-column or reagent well opening with a nozzle. For example, if the funnel assembly is arranged as a rectangular or square array, the treatment station must provide for nozzle arrays corresponding to the X-Y location of each inlet and outlet port for each column and well. The inlet end or loading port of each mini-column is press-fit disposed in a connection sleeve extending from the throat of a corresponding sample loading funnel of the funnel assembly. The taper of the inlet port of the mini-column is coplanar with the taper of the conical bottom of the funnel so that there is a virtually seamless transition from the funnel to the inlet port of the mini column. This will ensure that no dead volume exits that might lead to possible cross-contamination. Alternately the mini-column may be integrally cast as an extension of the loading funnel. In the first embodiment, once the sample on the column has been treated, the column may be removed for insertion into the high pressure line of an external HPLC analyzer such that the mini-column is now the support column for the HPLC. This is contrasted to the column of the prior art wherein the mini-column is merely a pre-column, requires an adapter, and does not supplant the standard HPLC column. Alternately, an HPLC analysis capability may be built into the system of this invention. In this case, the mini-columns need not be removed from the cassette and may be remain in place after treatment of the sample. The same nozzle interface used to address each column now acts as part of the high pressure line for an integrated HPLC.

In order to ensure the mini-columns remain press-fit connected to the funnel assembly and to ensure that each mini-column is aligned with the axis of symmetry of its corresponding funnel, an alignment means is optionally provided. The alignment assembly of the cassette of this invention ensures that the longitudinal axis of all mounted mini-columns are coincident with the longitudinal axis of its corresponding loading funnel. Proper alignment is essential, as will be explained below, to ensure that both the inlet port and outlet port of each mini-column is properly aligned to receive the distal ends of dispensing and expending nozzles although self-centering is achieved by virtue of the generally concave, preferably tapered openings. Where the mini-column is not integral to the funnel assembly, an alignment assembly may be provided. Once each mini-column has been inserted into the funnel assembly, the alignment assembly is positioned over the outlet ports of the mini-column. The alignment assembly is aligned with and removably attached to the funnel assembly as a spatial reference. Precisely spaced through-holes having a tapered inner bore are positioned on the alignment assembly to mate with the tapered shoulder of outlet port of each mini-column. Each mini-column is now secured on each end, thus holding each mini-column in proper alignment. Alternately, an extended sleeve maybe cast as part of the funnel assembly so that insertion of the mini-column into the extended sleeve will result in a stable or robust alignment as well as providing sufficient press fit of the mini-column to prevent the mini-column from falling out.

Where the mini-column is an integral part of the funnel assembly, bracing sufficient to ensure alignment of the mini-columns may cast as part of the integrated funnel assembly. For example, cross-bracing extending from the external wall of the integral mini column to the funnel assembly will provide a stable or robust alignment of the mini-columns.

A novel feature of this invention is the optional integration of a plurality of reagent wells into the funnel assembly. The reagent wells are open on each end and are supplied with frits, as in the mini-columns, to prevent material contained in the wells from falling out. The reagent well may be packed with a suitable support for immobilizing the specific reagent contained therein. Alternately, the reagent may be in powdered form either as a soluble solid or as a lyophilized solid. The solid reagent may be provided as a microencapsulated reagent (this would permit use of liquid reagents without having to provide a solid support), as beads of a predetermined size to permit solvent flow through and/or controlled solubility rates, or, alternately, the solid reagent may be painted on the walls of the column chamber, thus permitting the free flow of solvents.

Alternately, the reagent wells may be used as an alternative way to introduce samples for chemical treatment. By packing the wells with a suitable solid support, sample may be immobilzed on the support. This would effectively double the number of samples available on the cassette for treatment. Sample in other forms, such as adsorbed, lyophilized, powdered, microencapsulated, or free liquid, may be placed in the sample columns. Scanning the reagent wells with a scanning means will identify populated wells whose contents might participate in the predetermined chemical protocols.

As in the mini-columns, the ends of the inside chamber of the reagent wells are generally concave, and preferably tapered to provide a flared opening to permit the pressure tight seating of the distal ends of a dispensing and expensing interface means. These interface means include the same means discussed supra; e.g., nozzles having rounded or conical shaped tips. Once the fully assembled and loaded cassette assembly is inserted into the treatment system of this invention, each column and well opening is addressed by a nozzle. The tip of the nozzle is of a geometry designed to fit within the generally concave, preferably tapered openings of each mini-column and reagent well, and provide a tight seal thus achieving near-zero dead volume resulting in minimizing the risk of cross-contamination. In contrast, the prior art systems, which have no nozzle interface, or other direct flow-through communication interface, has a significant amount of dead volume. A novel feature of this invention is that the benefit of a funnel is attained for sample loading, however, near-zero dead volume is attained as well by the use of the nozzle interface. In accordance with the preselected chemical treatment protocol identified for a particular cassette, the nozzles permit the free flow introduction of a solvent, treatment solution, or a sample-containing solution to the column or well with which it is in communication(dispensing) or for removal of a solvent, spent treatment solution, or sample containing solution from a column well with which it is communication (expensing).

Another novel feature of the cassette of this invention is that each cassette has a machine readable code disposed on the cassette that is read by an appropriate device in the treatment station to automatically indicate to the treatment station in which the cassette is loaded the exact chemical protocols required for the samples in the cassette. The code will optionally indicate whether or not reagent is present in the reagent wells, whether the reagent wells contain additional samples rather than reagent, and which column and well addresses are to be treated (in the event that not all column and well addresses are populated). Alternately, a scanner can scan each column and/or reagent well to identify those column and reagent addresses that have material; i.e., solid support, reagent, solvent. Accordingly, empty columns and wells are not addressed and only those populated columns and wells identified by the scanner means participate in the identified chemistries. Scanning means suitable for identifying populated mini-columns and reagent-wells include either a light array having a single source or a plurality of sources and complementary light source detector array, or a mechanical probe inserted into the mini-column and reagent well openings to sense the presence of an obstruction such as a frit. In the preferred embodiment, the light source array is positioned over the mini-column and reagent well ports while the detector is positioned to detect whether the light is transmitted through the mini-column or reagent well. Those "empty" mini-columns and reagent wells where the light is transmitted through the column or well do not participate in the identified predetermined chemical protocols.

The machine readable code may be in the form of a bar code, a magnetic strip, an embedded diode, or a semiconductor memory chip. The device used to read the code will necessarily depend on the format and medium of the code and may include a bar code reader, a magnetic strip reader, a radio transponder, or a data bus socket. The foregoing means for encoding as machine readable code the chemical protocol information and the scanning devices for reading the machine readable code are presented by way of example and not by way of limitation as any means whether optical, magnetic, electrical impulse, and the like may be employed to provide to the treatment station an indication of the desired chemical protocols. A further novel feature of the cassette of this invention is that once the cassette has been loaded into the treatment station of this invention the machine readable code is modified to indicate that the desired chemical treatment protocol has been performed. Such modification may include modifying the code so that it becomes unreadable by the scanning device, thus preventing execution of any treatment protocol. For example, a bar code may be disposed in a bar code holder that is slideably inserted in a receiving groove in the cassette. Once the bar code is read, the bar code holder may be repositioned in the receiving groove so that part of the bar code is positioned in a pocket in the cassette, thus obscuring at least a portion of the bar code, rendering the bar code unreadable. This will serve to prevent the cassette from being processed a second time. As a further example, in the case of the semiconductor memory, a CMOS or static RAM may be used to contain the required protocol instructions. Once the memory is read, the coded instruction set may be modified to indicate that the cassette has undergone the prescribed chemical protocols. An advantage of using a random access memory means is that the modification of the machine readable code may optionally include writing information to the memory to provide information as to date and time the protocols were executed, the name of the technician operating the system, any deviations to the protocol, addresses of the columns and wells, and parametric information such as reagent volumes, operating temperatures and pressures, and the like. Optionally this information may be later downloaded to a permanent information storage location.

The system of this invention includes the cassette assembly, a sample loading station, and a treatment station. By way of operation, the cassette assembly is loaded into the sample loading station and aligned in preparation of receiving the sample. An annular gasket is lowered onto the top rim of the sample funnel being loaded. The pressure resulting from mounting the loading ket is such that the mini-column associated with the instant sample funnel is firmly pressed against the funnel opening to ensure a water tight fit between the narrow end of the minim-column and the sample funnel connection sleeve up to about 40 psi. The outlet end of the mini-column is position over a drain tube. The sample solution is then pipetted into the first well. After the sample solution has been introduced, a pressure cap having a centrally disposed plunger is lowered over the gasket so that the plunger extends into the sample funnel. An annular shoulder on the plunger seats against the gasket to create an air tight seal up to about 40 psi. A port in the plunger permits an inert gas to pressurize the head space in the sample funnel thus forcing the sample solution into aid through the mini-column. Alternately, the sample solution may be forced into and through the mini-column by either providing a vacuum draw at the outlet end of the mini-column to suction the sample solution through, or the plunger on the pressure cap may directly push the sample solution through the mini-column; i.e., hydraulic pressure. As the sample solution passes through the mini-column, any lipophilic moieties are immobilized on the hydrophobic packing material. Similarly, if the packing material were hydrophilic, any lipophobic moieties would be immobilized in that case. Superfluous sample solution is expired through the outlet port into a drain line. The funnel is depressurized, and the plunger and gasket removed. This process is repeated for all sample funnel/mini-column addresses in the array.

Alternately a multi station sample loading device may be used whereby all sample funnel/mini-column addresses are loaded simultaneously. This embodiment, as well as the single station loading station embodiment, may optionally provide an sample dispensing port in the plunger(s) to automatically dispense the sample solution into the sample funnel well(s) after the plunger is seated. A further option includes a means for reading the machine readable code so that a microcontroller interface might load the cassette pursuant to a predetermined sampling protocol.

OBJECTS AND ADVANTAGES

It is an object of this invention to provide a cassette for a chemical treatment system having a plurality of funnels for loading sample solutions, a plurality of sample retaining means for holding a plurality of addressable, preselected samples and preselected reagents, to permit preselected chemistries on the preselected samples in a sequential interrupted fashion, the cassette having a machine readable code integrated thereon to automatically identify to the chemical treatment system upon insertion of the cassette into a chemical treatment station the chemistries to be performed on the preselected samples using the preselected reagents, the cassette having very near-zero dead volume flow-through connection with a chemical treatment station.

It is another object of this invention to provide a sample loading station not requiring pre-isolation of the sample in a reaction chamber and that will enable rapid loading of the chemical treatment cassette of this invention.

It is another object of this invention to provide an improved sample column for sample immobilization or containment and for insertion into the cassette of this invention to permit flow-through chemistries with near-zero dead volume and to permit access to and use of the improved sample column as an HPLC column without the need for a high-pressure adapter.

It is another object of this invention to provide a sample treatment station for receiving the chemical treatment cassette of this invention, for reading the machine readable code on the cassette, for uninterrupted, sequential accessing all pre-selected samples and pre-selected reagents, and for executing the chemistries as identified by the machine readable code.

It is another object of this invention to provide a chemical treatment system having a sample loading station, a chemical treatment cassette, and a chemical treatment station for performing automatic, near-simultaneous, flow-through chemistries on a plurality of pre-selected samples using a plurality of pre-selected reagents, the chemistries being identified by machine readable code to a micro-controller, and the chemistries being executed by the micro-controller working in logical and electrical cooperation with the chemical treatment station.

It is another object of this invention to provide a method for near simultaneous performance of chemistries an a plurality of preselected samples, the samples being retained in a chemical treatment cassette, and the chemistries desired retained on machine readable code for automatic execution via micro-processor control pursuant to instructions contained in the machine readable code.

Still other objects will be evident from the specification claims and drawings of this application.

BRIEF DESCRIPTION OF DRAWINGS

The invention is illustrated by reference to the drawings in which:

FIGS. 5a,b are cross-sectional views of the chemical treatment cassette of the chemical treatment system of this invention showing the relationship of the sample columns and nozzles with respect to each other and to other elements of the chemical treatment cassette;

FIG. 6 is a cross-section view of an equally preferred embodiment of the chemical treatment cassette of the chemical treatment system of this invention;

FIG. 7 is a cross-section view showing how the nozzle is seated in the tapered opening embodiment of the mini-columns and reagent wells of the chemical treatment cassette of this invention;

BEST MODE FOR CARRYING OUT THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Figure 1:
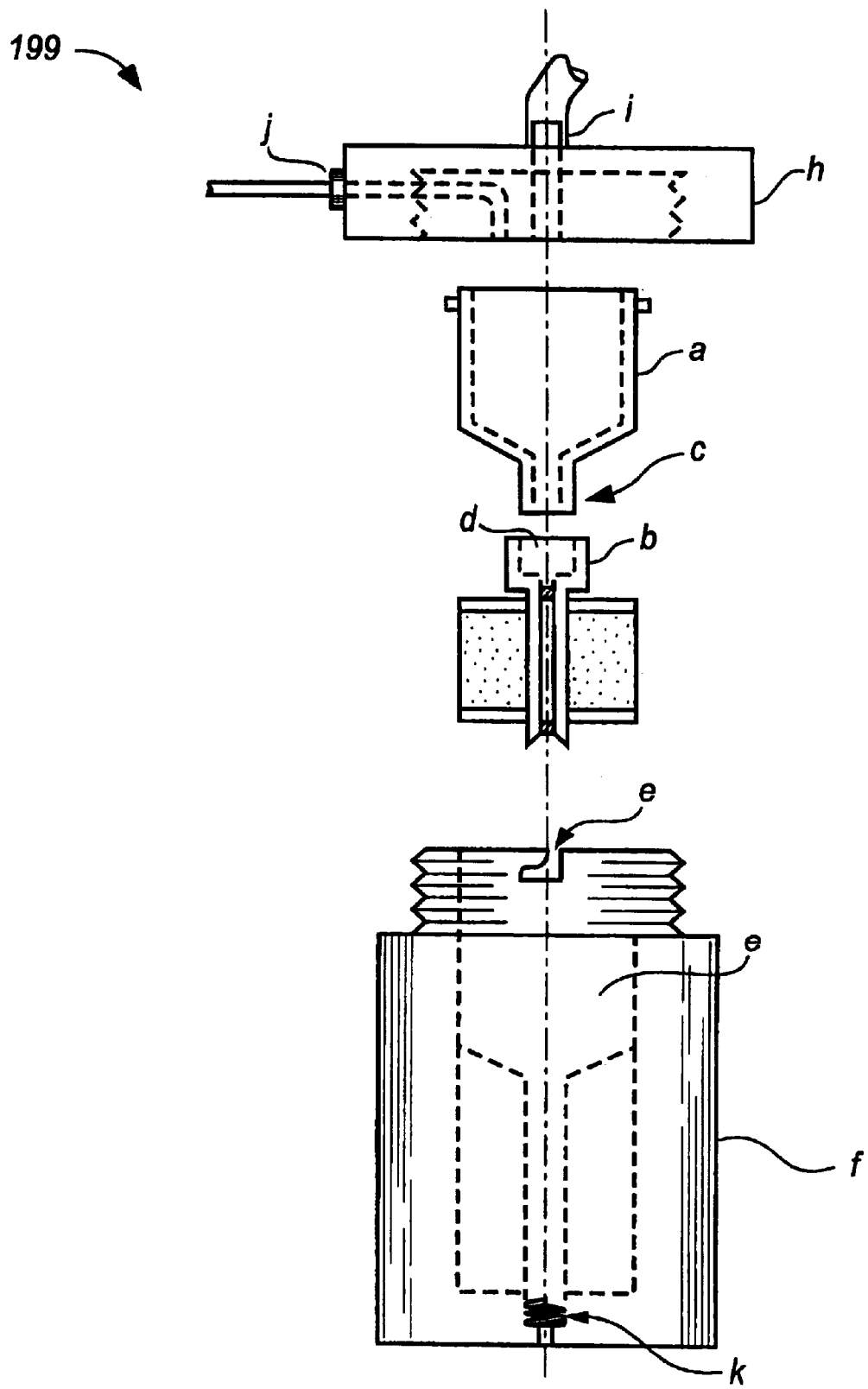
FIG. 1 is a cross-sectional diagram of a single-sample chemical treatment cartridge or reactor of the background art.
Figure 2:
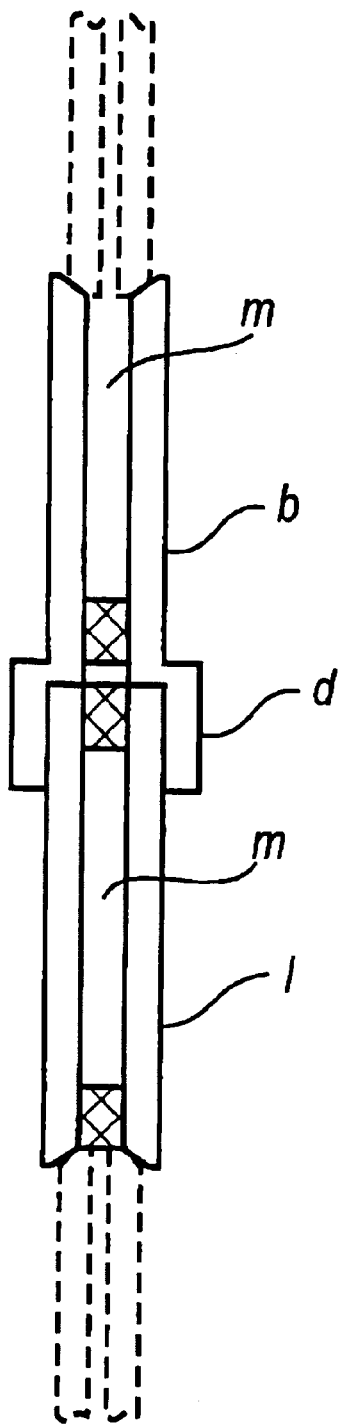
FIG. 2 is a cross-sectional diagram of the sample column of the background art as connected to an HPLC high-pressure adapter.
Figure 3A:
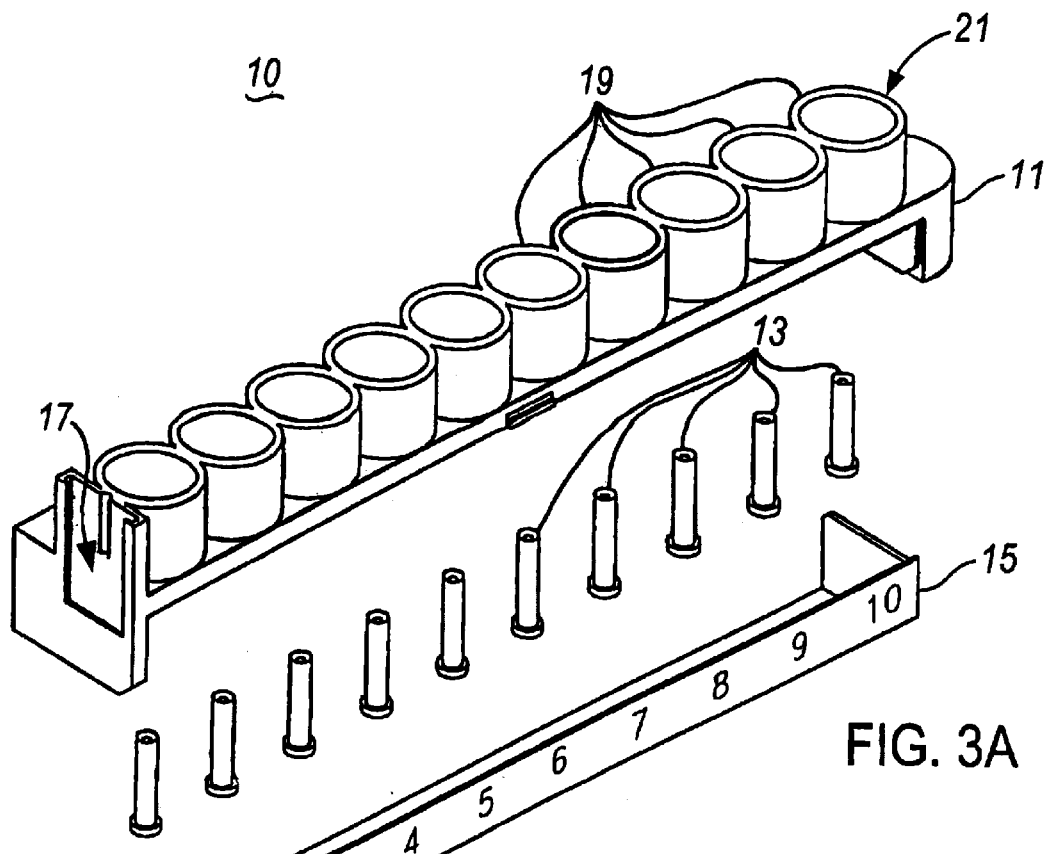
FIGS. 3a–e are various perspective views of the chemical treatment cassette of the chemical treatment system of this invention.

The three principle elements of the chemical treatment system of this invention include a sample loading station, a sample treatment station, and a chemical treatment cassette. Both the sample loading station and the chemical treatment station elements are configured in accordance with the geometry and configuration of the chemical treatment cassette (hereafter "cassette"). The preferred embodiment of the cassette is easily seen in the exploded view as shown in FIG. 3a. The principle elements of the cassette 10 include a sample funnel assembly 11, a plurality of mini-columns 13, a mini-column alignment assembly 15, and a receptacle for removably retaining a medium containing a machine readable code 17.

Figure 3B:
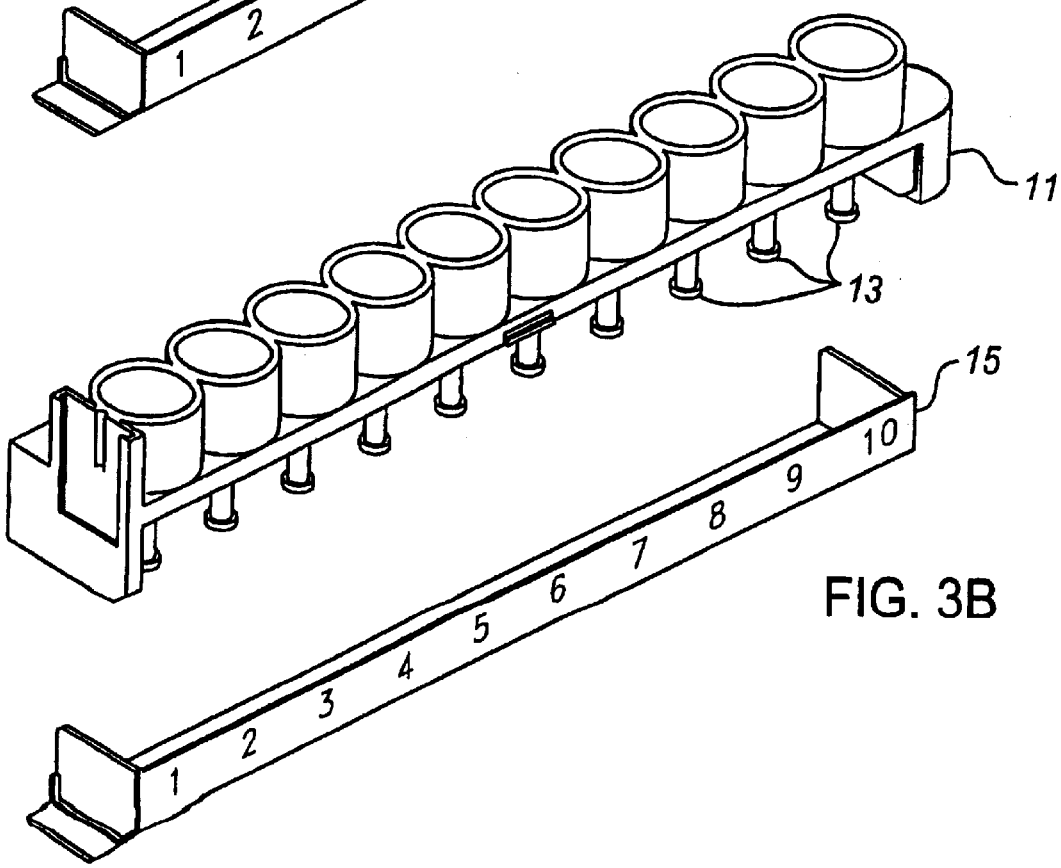
Figure 3C:
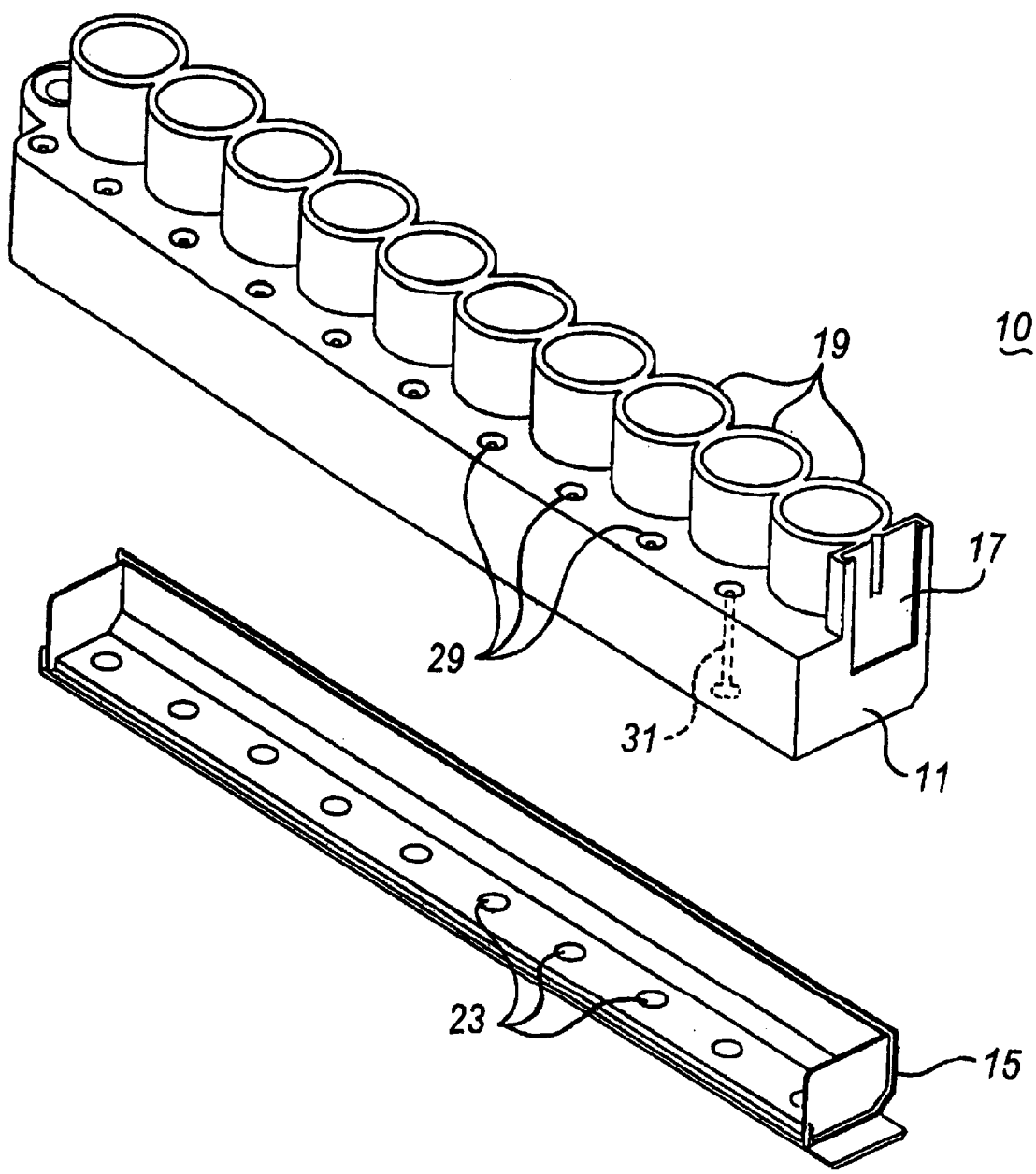

The sample funnel assembly 11 contains a plurality of funnels 19 integral to the assembly and arranged in a even, regular funnel array. FIG. 3a shows the sample funnel assembly as a linear array 21. FIG. 3b shows the mini-columns 13 inserted into the funnel assembly 11. The location of each mini-column may be stamped onto the alignment assembly 15 to facilitate sample loading and for tracking purposes. FIG. 3c is a mirror-image perspective view of FIG. 3b and clearly shows the plurality of through-holes 23 in the alignment assembly by which the flared, generally concave, preferably tapered, free end of the mini-column may be aligned for later connection and interface to a chemical treatment station. The alignment holes 23 are tapered so as to receive the tapered flange of the free end of the mini-columns and to self align the columns as the alignment assembly 15 is snapped into place.

FIG. 3c shows the inlet ports 29 of reagent wells 31, shown in phantom, that are integrated into the funnel assembly 11. As discussed above, the reagent wells may be used as a source of adsorbed, powdered, freeze dried, microencapsulated, and liquid reagents, solvents, salts, buffers, or other chemicals participating actively or passively in the chemistry performed on the samples in the mini-columns.

Figure 3D:
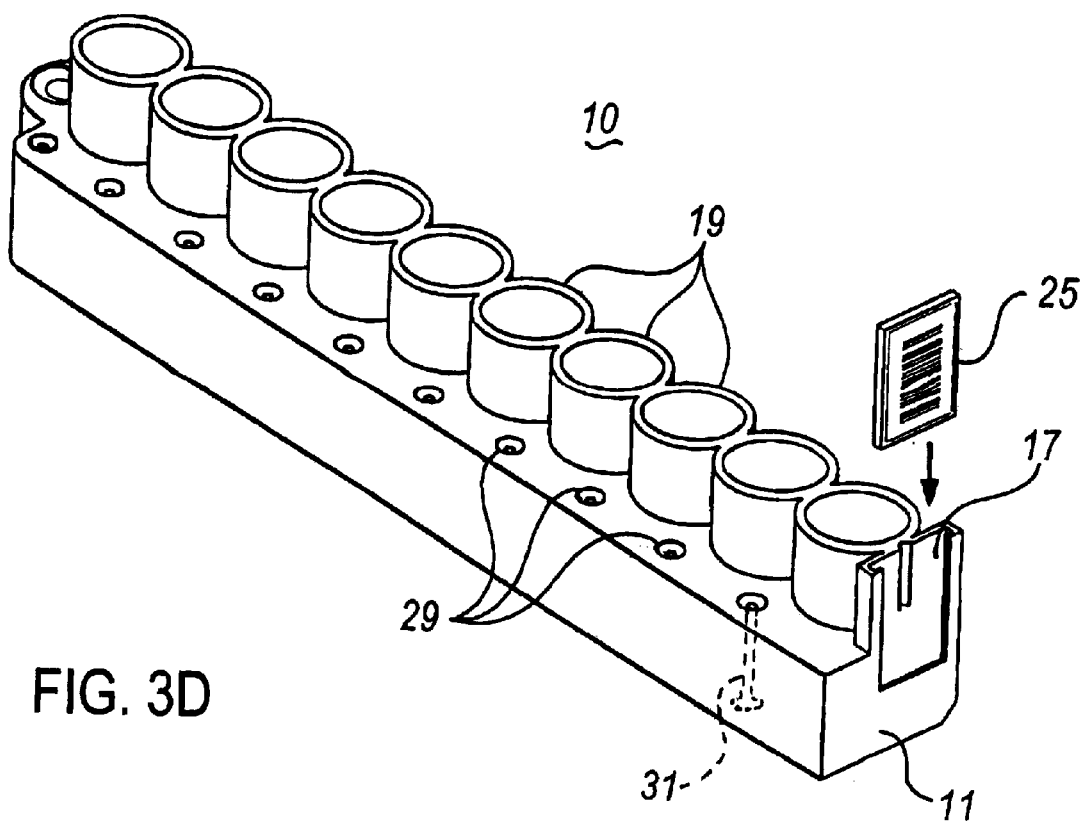
Figure 3E:
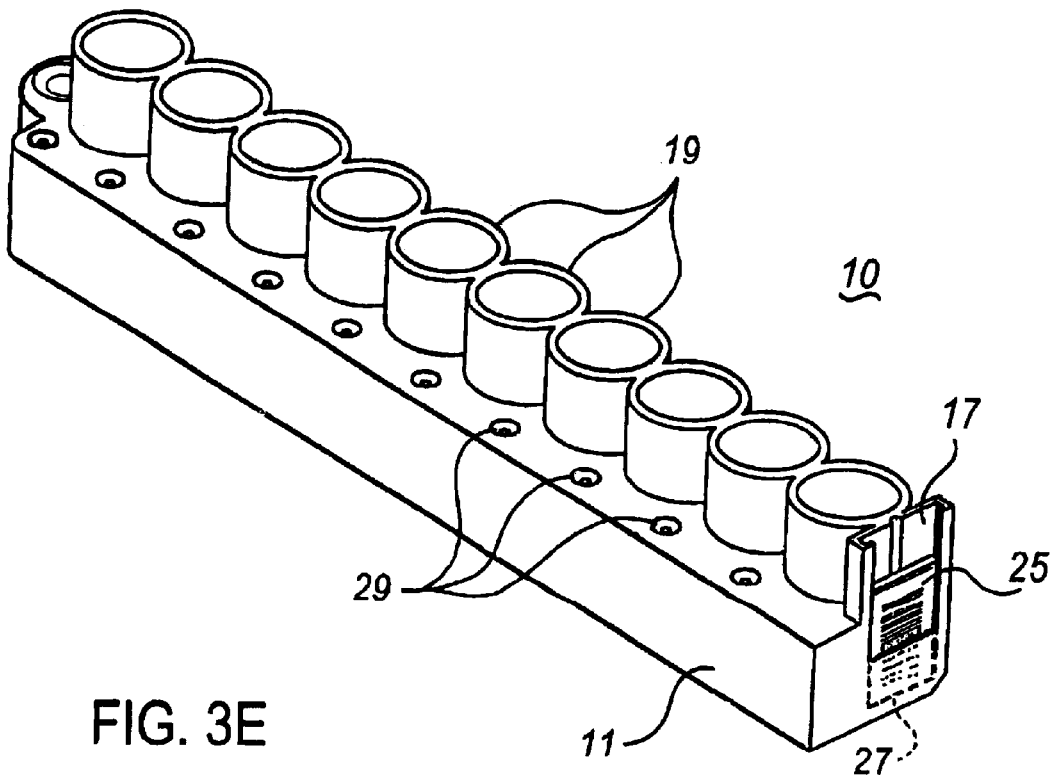

Also shown in FIG. 3c is the receiving slot 17 for the machine readable code means. In the preferred embodiment of the cassette of this invention the machine readable code means is a bar code. FIG. 3d shows how a bar code 25 is inserted into the receiving slot 17. FIG. 3e shows the bar code 25 slideably received in the receiving slot. As shown in phantom, the bar code 25 has been displaced to the extreme bottom end 27 of the receiving slot 17 rendering the bar code unreadable. A mechanism is provided in the treatment station of this invention to displace the bar code to the extreme bottom end of the receiving slot once the cassette has been addressed by the interface nozzle arrays contained in the treatment station by which the flow-through chemistry is effected, thus preventing the cassette from being used again.

Figure 3F:
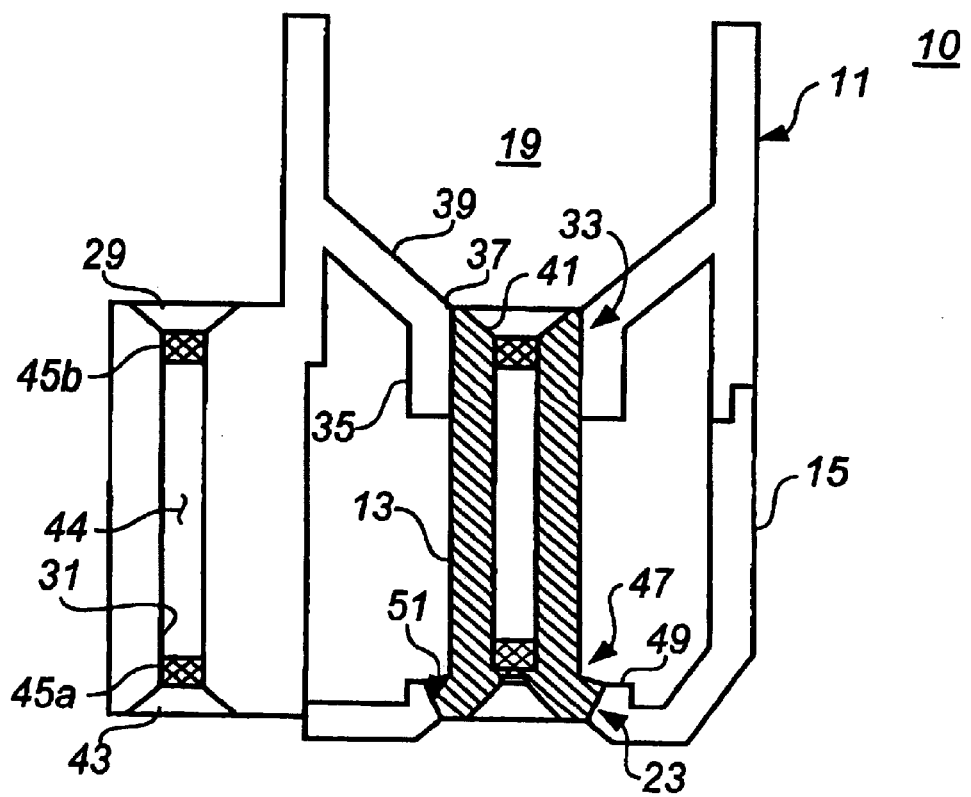
FIG. 3f is a cross section view of the multiple sample, chemical treatment cassette assembly of this invention.

A cross-section view of the chemical treatment cassette assembly is shown in FIG. 3f which clearly shows the inter-relationships between the various elements of the cassette assembly. The sample mini-column 13 has a first narrow end 33 which is press-fit into a mini-column connection sleeve 35 formed by extending the throat of the sample funnel 19. A stop shoulder 37 disposed annularly on the funnel end of the inside wall of the connection sleeve 35 provides a stop barrier to prevent the mini-column 13 from extending into the cavity of the funnel 19 and provides a sealing surface between the inlet port of the column and the throat of the funnel to prevent sample solution from leaking during sample loading. Further, the stop barrier extends over the edge of the mini-column narrow end 33 by an amount sufficient to provide a smooth transition from the sloped inside wall 39 of the funnel to the generally concave, preferably tapered wall 41 of the narrow end of the mini-column. This smooth transition from funnel to mini-column reduces the risk of sample or wash solvent residues forming on what would otherwise be a surface irregularity. Such residues may lead to errors and significantly affect the results of the chemistries involved.

FIG. 3f also clearly shows the structure of the reagent wells 31. The wells have an inlet port 29, and an outlet port 43. A center chamber 44 runs longitudinally through the reagent well and connects the inlet port 29 with the outlet port 43 within which chamber may be disposed any reagents, solvents, buffers salts, enzymes, and the like, in either an adsorbed, powdered, lyophilized, microencapsulated, or liquid state, useful in the chemistries associated with the sample that is retained by the sample mini-column 13. Inert porous frits 45a and 45b are press fit into the ends of the central chamber to prevent loss of the materials contained in the reagent well central chamber.

Figure 4:
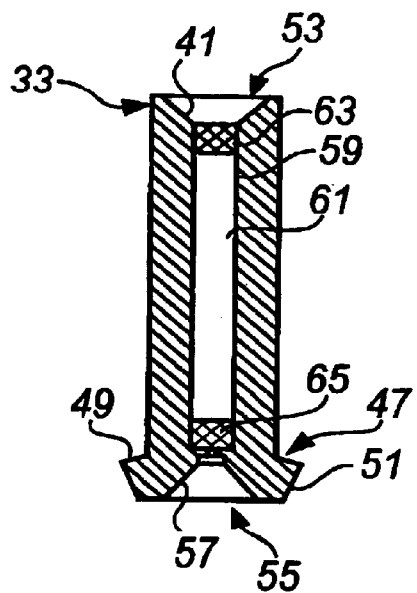
FIG. 4 is a cross-sectional diagram of the sample mini-column of this invention.

FIG. 3f also clearly shows how the flange 49 of the flanged end 47 sample mini-column 13 is seated in the through hole 23 of the alignment assembly 15. The outside annular edge 51 of the flange 49 is tapered so that it mates with the taper of the inside wall of the through hole 23. Once the alignment assembly 15 is snapped into place with the funnel assembly 11, the mini-column is held in an aligned position stable enough to move and manipulate the cassette assembly 10 without loosening the mini-columns 13 from their connection sleeves 35. The mini-column 13 of this invention is shown more clearly in FIG. 4. It is comprised of a narrow end 33, a flanged end 47 having an annular flange 49 outwardly extending from the flanged end 47. The outside annular edge 51 of the flange 49 is tapered inwardly so as to be accommodated by and self-centering in an alignment hole 23 of the alignment assembly 15, the alignment hole also having a complementary tapered bore for receiving the outside tapered mini-column flanged end 47. A longitudinal chamber 59 connects a narrow end inlet port 53 with a flanged end outlet port 55. Both the inlet port 53 and the outlet port 55 have a bores 41 and 57 to facilitate leak-proof, high pressure seal with a nozzle interface of the chemical treatment station of this invention or external analyte analyzer. The chamber is typically packed with a solid support material 61 such as silica that has been derivatized with a lipophyllic polymer (e.g., a C18 compound) thus rendering the support hydrophobic. Other support materials may be used including polymer or resin beads, cellulose, and the like. Further, depending on the sample to be immobilized, the support may be made hydrophillic. The support material is retained in the column by porous frits 63 and 65. These frits may be made of any inert porous material including sintered polyethylene, polypropylene, fluoropolymers, glass, and the like.

FIG. 5a is an exploded, cross-section view of the chemical treatment cassette assembly 10 showing how the nozzles of the chemical treatment station interface addresses the cassette. Each address of the cassette includes a reagent well 31 with an inlet port 29 and outlet port 43, and a sample mini-column 13, also having an inlet port 53 and an outlet port 55. As is clearly shown in FIG. 5a, a mini-column inlet nozzle 67 interfaces with the mini column inlet port 53 by seating the nozzle tip 68 against the generally concave, preferably tapered bore 41 of the mini-column inlet port 53. The nozzle 67 contains a through-bore 69 disposed on the longitudinal axis of the nozzle, the through-bore having a rounded, polished distal end 68 in communication with the inlet port 53 of the mini-column through which solutions and solvents are either introduced to or removed from the mini-column.

Similarly, the mini-column outlet nozzle 73 interfaces with the mini-column outlet port 55 by seating the rounded, polished nozzle tip 74 against the generally concave, preferably tapered bore 57 of the mini-column outlet port. The nozzle 73 contains a through-bore 75 disposed on the longitudinal axis of the nozzle, the through-bore terminating at the rounded, polished distal end 74 to provide communication with the outlet port 55 of the mini-column through which solutions and solvents are either introduced to or removed from the mini-column.

Similarly, the reagent well inlet port 29 interfaces with a reagent well inlet nozzle 78 having the same structure as the mini-column inlet port nozzle 67, and the reagent well outlet port 43 interfaces with a reagent well outlet nozzle 79 having the same structure as the mini-column inlet port outlet nozzle 73, to enable hydraulic and pneumatic communication of the reagent well with the chemical treatment station.

Note that other interface means may be used including slip fittings, threaded fittings, gasketted butt-joint fittings, and the like, however, the preferred embodiment uses the nozzles as described above. FIG. 5b shows the nozzle tips inserted into the generally concave, preferably tapered bored openings of the mini-column and reagent well inlet and outlet ports. FIG. 7 is a detailed cross-section view of the nozzle tip 74 of the mini-column outlet port nozzle 73 seated in the mini-column outlet port 55, and typifies the nozzle/port interface of this invention. The rounded, polished end 74 of the nozzle 73 is urged or pressed against the generally concave, preferably tapered wall 57 of the outlet opening 55 with a pressure sufficient to provide a leak-proof, seal between the tapered opening and the nozzle tip. The seal between the reagent well and the reagent well nozzles must withstand up to 40–50 psi, whereas the mini-column seals must withstand pressures in excess of 1500 psi. The mini-column/nozzle interface must withstand these higher pressures to provide in-line HPLC capability.

The advantage of the column/nozzle interface over the background art is easily discerned. A significant amount of dead volume is introduced by the system of the background art since the walls of their sample funnel provide an extensive surface area on which residues and other contaminants might collect. These residues pose a significant cross-contamination threat where multi-step chemistries are performed on less than milligram quantities of sample. By eliminating the sample funnel as a means for dispensing reagents and solvents to the mini-column (as in the background art) the interface of this invention achieves a near-zero dead volume since there are no surfaces on which residues of prior solutions might collect, while still obtaining the benefit of the funnel for sample loading.

FIG. 6 is a cross-section, exploded view of an equally preferred chemical treatment cassette assembly wherein the mini-column 14 at each address is integral to the sample funnel assembly. This embodiment is preferred when, for example, the chemical treatment station is capable of performing on-board, in-line analysis of the reacted sample, thus vitiating the need to remove the sample mini-column from the chemical treatment cassette (in order to perform off-line analysis of the reacted sample immobilized on the column). This embodiment requires no alignment assembly as each integral column is prealigned and permanently affixed in place. Further, this embodiment permits the mini-column inlet and outlet nozzles to act as the high-pressure interface connection with the on-board analyzer, typically HPLC, thus elinating the need to have a separate analyzer dock with a separate interface assembly in the chemical treatment station.

Figure 8:
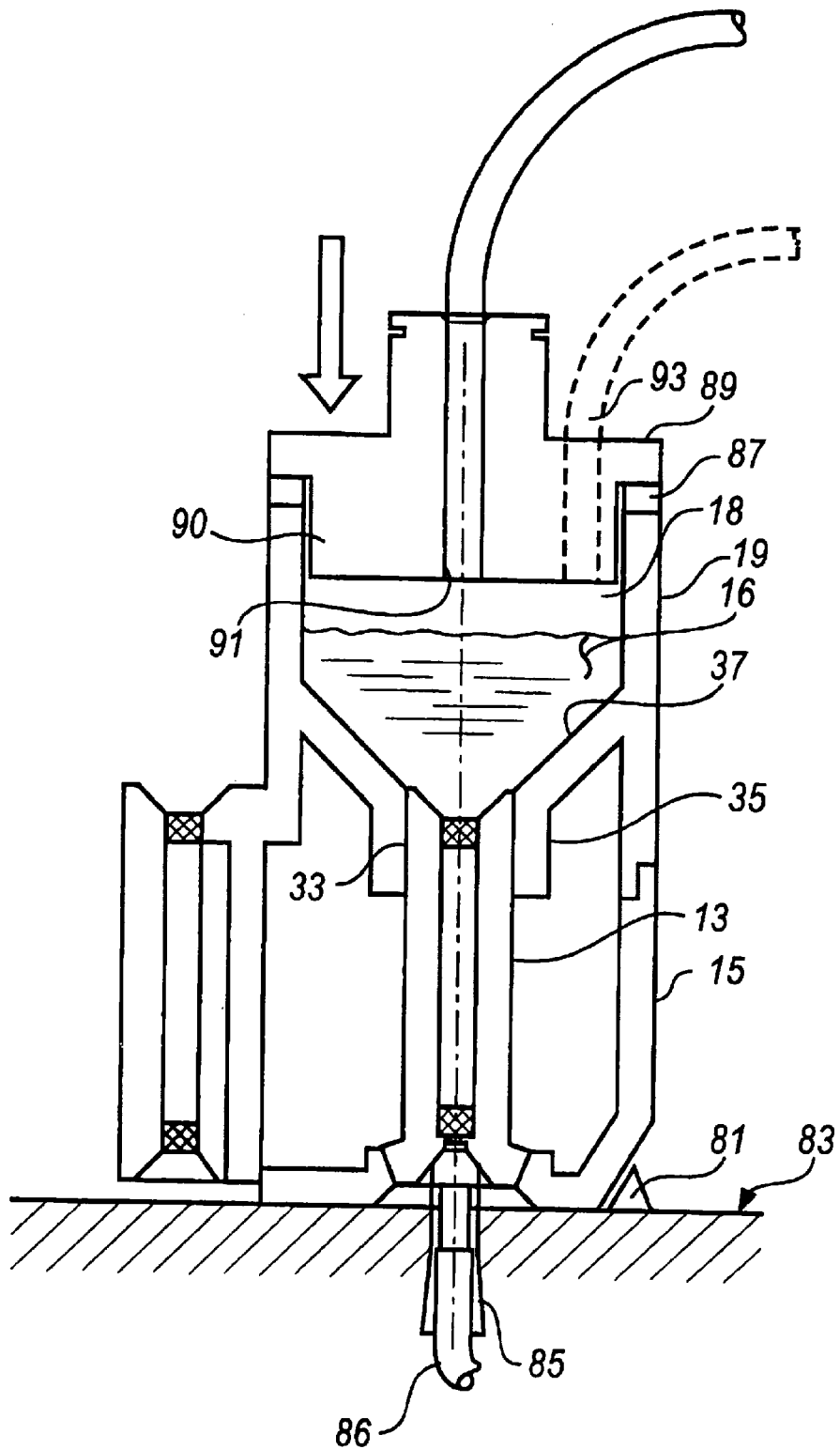
FIG. 8 is a cross-section view of the chemical treatment cassette as loaded in the sample loading station.

The loading station of this invention comprises an X-Y alignment means, a gasket loading means and a plunger or pressure cap means. FIG. 8 is a cross-section view of the chemical treatment cassette of this invention in the sample loading station. The cassette is positioned so that the gasket and pressure cap will precisely engage the sample funnel. FIG. 8 shows the cassette positioned via an alignment means shown diagramatically as an alignment pin 81 extending upwards from the loading platform 83. A plurality of alignment pins may be positioned on the platform to permit precise positioning of the cassette assembly. Alternately, the cassette may be locked onto a slideable platform having predetermined stops to permit the precise positioning of each sample well 19 for single sample loading. Alternately, an alignment stop having a shape complementary conforming to the external shape of the funnel assembly may be used to position and index the individual funnels during sample loading. Once positioned, an annular gasket 87 is positioned over the sample well and a sealing gasket actuator lowers the sealing gasket 87 over the sample well, 19 and a seal is made by exerting a downward pressure on the gasket to provide a pressure seal. The pressure seal also serves to urge the mini-column outlet port against a drain interface 85 thus providing a seal between the outlet port and the drain interface, and to urge the narrow end 33 of the mini-column 13 against the annular shoulder 37 in the connection sleeve 35, thus providing a pressure seal between the sample funnel 19 and the mini-column. Next, the sample solution 16 is introduced into the sample funnel 19. The pressure cap 89 is then lowered onto the gasket and pressure applied to provide a seal between the pressure cap and the gasket. A centrally disposed plunger 90 on the pressure cap extends into the funnel 19. Inert gas is then introduce into the head space 18 between the sample solution and the plunger 90 via a gas entry port 91 disposed in the pressure cap, thus forcing the sample solution 16 through the mini-column 13 with the excess solution passing through the mini-column and drained away through the waste tube 86 connected to the drain interface 85. Once the sample solution has passed through the column, the inert gas pressure is released, and the pressure cap and gasket are removed. The cassette is then repositioned for sample loading of the funnel at the next address, or optionally, either a second sample solution or a wash solvent may be loaded. This process is repeated until all the mini-columns at the desired addresses have been loaded. It should be noted that the loader of this invention does rot require that the sample funnel or the cassette be inserted in a special reaction chamber or holder in order to load the mini-column as is done in the background art. Further, the novel aspects of the loader of this invention may be extended to a multiple sample loading station whereby more than one address may be loaded with an sample at a time. Also, an optional sample introduction port 93 may be provided in the pressure cap so that the gasket 87, which serves to pressure seal the mini-column with the funnel prior to introduction of the sample, may be eliminated since the pressure cap will now provide the force required to seal the mini-column against the funnel and the sample is not introduced into the funnel until after the pressure cap is in place.

Figure 9:
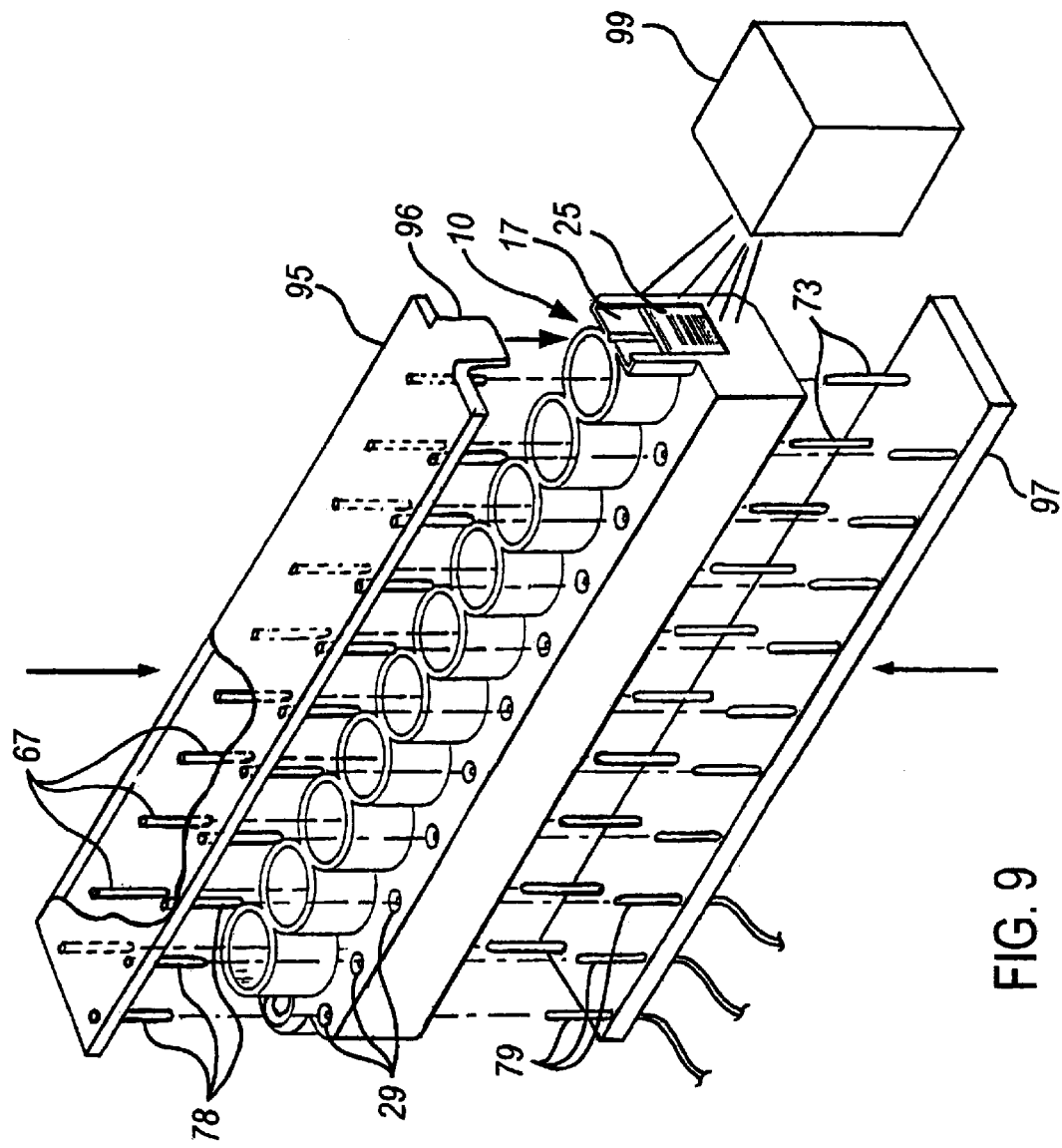
FIG. 9 is a perspective view of the chemical treatment cassette and the upper and lower nozzle arrays of the chemical treatment station and their relative positions spatial positions prior to loading the nozzles into the sample column and reagent well generally concave, preferably tapered openings.

After the chemical treatment cassette has been loaded it is inserted into the chemical treatment station (CTS) of this invention. The CTS positions the cassette so that the cassette/CTS interface can be established. Positioning of the cassette is performed automatically by means well known in the art. FIG. 9 is a diagram showing the cassette 10 position between the nozzle interface arrays 95 and 96. After insertion into the CTS, the bar code 25 is read by a bar-code reader 99. The instructions contained in the bar code are sent to a micro-controller and the appropriate algorithm is accessed and loaded for execution of the process steps and chemistries indicated by the bar code instructions. Once the cassette is transferred into position, interface nozzle arrays 95 and 96 are brought together and into contact with the cassette so that the tips of the nozzles 67, 78, 73, and 79 are brought into pressure contact with their respective mini-column and reagent well ports. As the nozzle arrays are brought together, the bar code 25 is disabled by action of a tab or pin 96 on the slideable bar code forcing it to a position in the bar code receiving slot 17 where the bar code is at least partially obscured. Once the nozzle/cassette interfaces have been established the materials in the reagent wells and the immobilized sample in the minicolumns are now accessible to the CTS so that the predetermined chemistries can be performed.

Figure 10B:
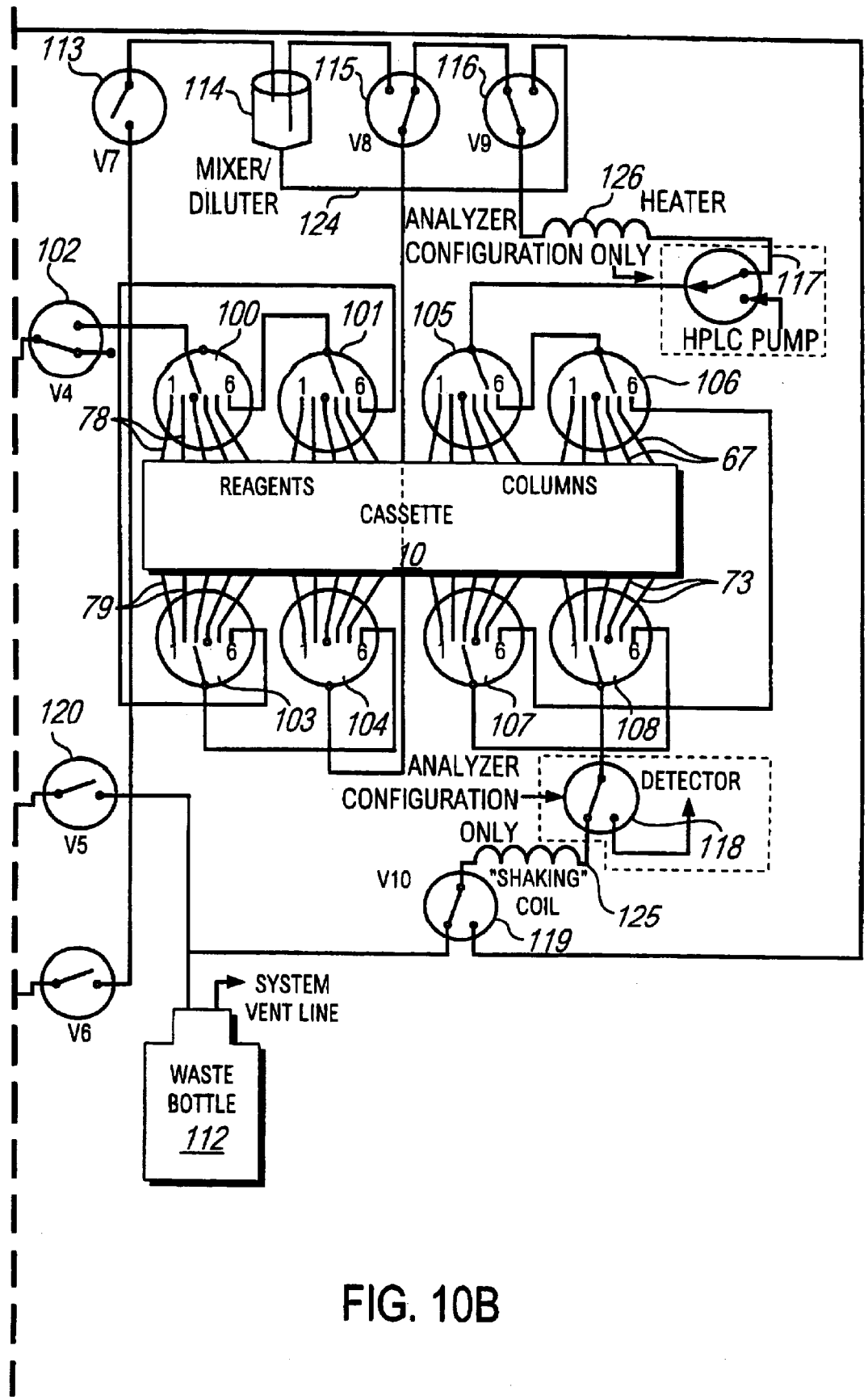
FIG. 10 is a schematic overview diagram of the hydraulic layout of the chemical treatment station of this invention.

The preferred embodiment of the CTS of this invention is shown schematically in FIG. 10. The loaded chemical treatment cassette is depicted as being addressed by the nozzle array interfaces. The mini-columns are addressed by the mini-column inlet port nozzles 67 and outlet port nozzles 73, and the reagent ports are addressed by inlet nozzles 78 and outlet nozzles 79. Each reagent well may be selected individually for processing by adjustment of rotary valves 100, 101, 103, and 104, and each mini-column may be selected individually by the appropriate adjustment of rotary valves 105, 106, 107, and 108. Note that rotary valve inlet and outlet pairs; i.e., 100 and 103, 101 and 104, 105 and 107, and 106 and 108, are synchronized so that when the inlet port of a reagent well or a mini-column is selected, the rotary valve for the outlet port may only be set to that reagent well or mini-column.

Solvents, reagents, buffers, and other solutions are supplied from up to six reagent bottles 111*a*–*f*, with the desired reagent being selected by appropriate adjustment of the solvent valve blocks 109 and 110, and by appropriate selection of pressure switch from the pressurized valve blocks 122 and 123. These reagents are in addition to the reagents supplied in the reagent wells of the cassette. All solvents must pass through valve V4 102. Default position for all solvent and reagent rotary valves is set to direct the reagents to waste 112.

Reagents 111*a*–*f* may be directed to the mini-columns by closing valve V 102. This will direct the selected reagent to the mini-column inlet selected by the rotary valves 105 and 106 with any waste reagent passing through valve 118, valve 119 and into the waste bottle 112.

Solvents may be directed to the reagent wells for rehydration or salvation of adsorbed, powdered or lyophillized reagents in the reagent wells by switching rotary valve V4 102. Solvent is now directed to reagent cell inlet rotary valves 100 and 101. Note that position 6 of the reagent well and mini-column rotary valves is a pass-through position. Thus if rotary valve 100 is set at position 6, the solvent will pass through to the reagent selected by rotary valve 101. If desired. the solvent may be passed-through and stored in the mixer-diluter 114 by closing valve V8 115 and V4 102. This permits mixing various reagents and solvents with one another, including solvated dry reagents from the reagent wells of the cassette, prior to moving the mixture through line 124, valve 117 and valve 116, and to the mini-column rotary valves 105 and 106 for reaction with the immobilized sample.

The CTS of this invention provide three areas where solvent, analyte or sample solutions may be stored. These areas include the mixer diluter which, as described above, permits solvents and reagents to be mixed prior to reaction with the samples or analyte. Reagents, sample and analyte may also be accumulated (i.e., temporarily stored) in the heater coil 126 and in the shaking coil 125. It may be desirable to remove the sample or analyte from the support packing in the mini-column for a number of reasons. For example, where the hydrophobic support results in a conformational deformation of a protein or peptide side chain or otherwise affects the reactivity of the peptide or protein side chains, it might be desirable to perform the desired reaction external to the column. In this event, a suitable lipophobic solvent is used to detach the protein from the support. Valves V10 119, and valve 117, and 116 are closed resulting in the sample or analyte, now in solution, to be forced out of the inlet port of the affected mini-column, through valve 117, heater coil 126, valve 116 and into the mixer/diluter 114 wherein the desired reaction chemistry may be performed with reagents already present, or introduced later. As another example, detaching the sample may be desirable in the event the characteristics of the support material must be changes; e.g., changing it from a hydrophobic support to a hydrophillic support in the middle of the chemistry being automatically executed by the CTS.

The CTS of this invention is able to mix solvents, reactants and buffers; to detach and shuttle the sample back and forth (i.e., pump-up and pump-down; to perform complex chemistries either on or off-column; and to solvate adsorbed, powdered or lyophillized reagents, all performed automatically, pursuant to instructions indicated to a micro-controller by a bar code, without having to remove the cassette from the CTS, without having to detach or reattach the CTS/cassette interface, or otherwise require human intervention. Further, the same chemistries may be performed on all sample mini-column addresses, or a separate completely independent set of protocols may be defined for each address, or for each block of addresses.

Figure 11:
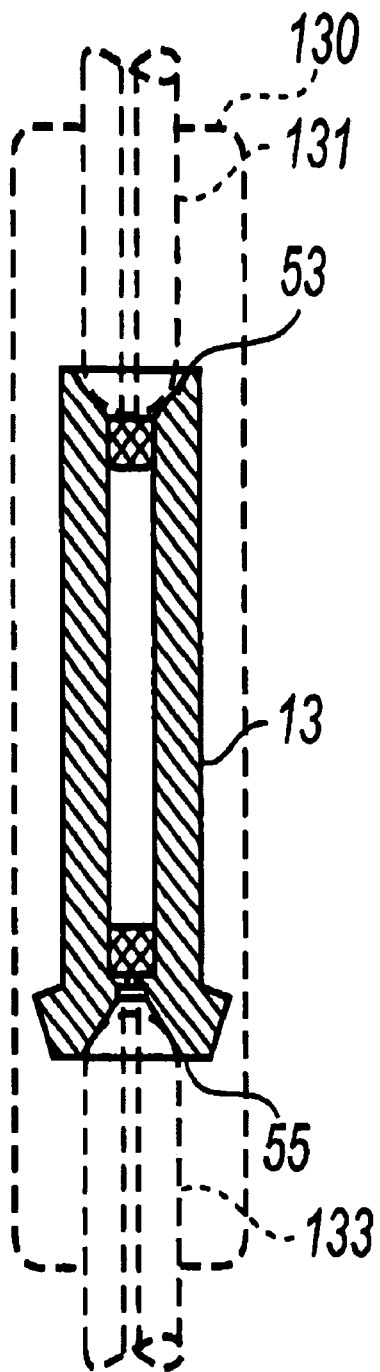
FIG. 11 is a cross-section diagram of the mini-column of this invention being in an HPLC in-line adaptor.

Further, an optional analyte analysis capability may be included in the CTS of this invention. Any of the mini-columns may be converted to an in-line HPLC column, by switching rotary valve 117 to receive solvent from an HPLC pump and by switching rotary valve 118 to direct the eluant to a detector. It is clear that the CTS is capable of performing a variety of analysis other than HPLC without having to remove the cassette from the CTS. However, if on-board, in-line analysis is not available, the mini-column may be removed from the cassette and directly inserted into an in-line, high-pressure adapter as shown in FIG. 11. The adapter 130 receives the mini-column 13 containing the analyte. Nozzles 131 and 133 are seated against the generally concave, preferably tapered inlet port 53 and outlet port 55 to form a high pressure seal. The mini-column of this invention does not require that a separate column/adapter be provided in order to accommodate in-line HPLC.

Figure 12:
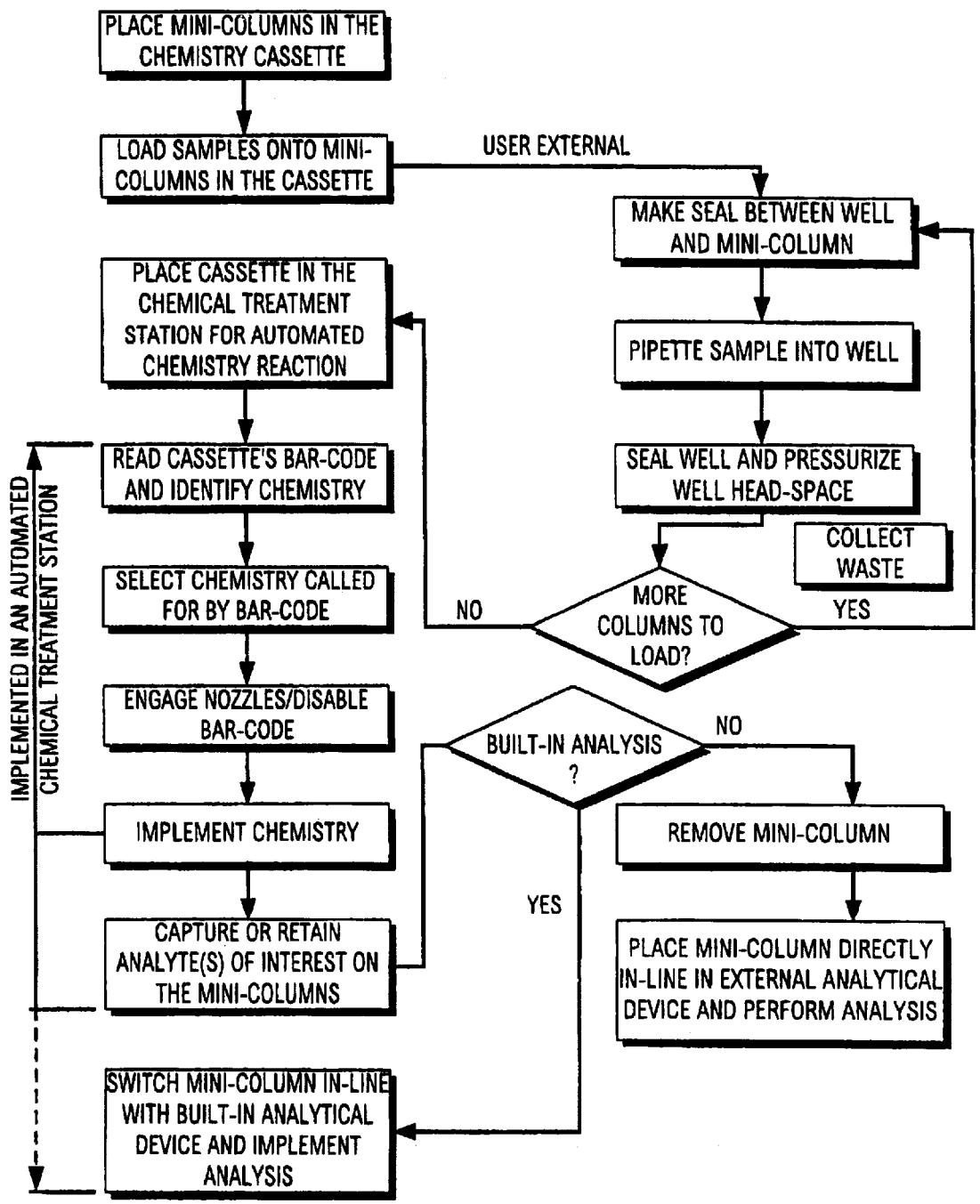
FIG. 12 is a flow diagram of the method of using the chemical treatemnt system of this invention.

The process of this invention as described supra beginning with the loading of the cassette, followed by execution by the CTS of the selected chemistries as predetermined by the instructions contained on a bar code affixed to the cassette, and concluding with either in-line onboard analysis, or an improved external analysis is summarized in FIG. 12.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

I claim:

1. A chemical treatment system for sequential, uninterrupted treatment of less than milligram quantities of a plurality of chemical samples, comprising in operative combination:

a) a chemical treatment cassette for retaining a plurality of chemical samples for chemical treatment, said chemical treatment cassette further comprising:

i) a funnel assembly comprising a plurality of integrated, individually addressable chemical solution sampling funnels for receiving chemical sample solutions, each of said sampling funnels having a first, open mouth end for introduction of a chemical sample solution, and a tapered, second conical end having a through-hole at the apex of said conical end, said sampling funnels being arranged in an array to permit individual addressing for chemical treatment;

ii) a plurality of sample mini-columns for retaining preselected chemical samples, each of said mini-columns having a centrally disposed chamber extending longitudinally through said mini-column, at least one of said mini-columns having a material selected from at least one of a solid support, dry reagent, dry sample, liquid reagent, liquid sample, and porous frits disposed in said central chamber, said chamber terminating into a first open end, said first open end having a flared, tapered inlet port, said inlet port being in flow-through, physical connection with said through-hole in said conical second end of said funnel, said connection resulting in smooth, continuous transition of the taper from said conical second end of said funnel to said taper of said inlet port, said chamber terminating into a second open end, said second open end having a flared, tapered outlet port, said outlet port being in flow-through communication with said inlet port, said first open end of each of said funnels and said tapered conical second end of each of said funnels and permitting localized access by a compressive fit interface to said mini-column inlet port for near-zero dead volume flow-through communication between said interface and said mini-columns;

iii) at least one reagent well for retaining preselected reagents for reaction with said preselected sample retained in said min-columns, said reagent wells comprising a through-bore parallel to said longitudinal axis of said mini-column, said through-bore terminating in a first end having a flared, tapered inlet port, and terminating in a second end having a flared, outlet port said reagent well inlet port being in flow-through communication with said reagent well outlet port; and iv) a machine readable code disposed on said chemical treatment cassette for identifying the chemistry protocols to be performed on the retained samples in said mini-columns;

b) a sample loading station for loading sample solutions in said sample funnels, said sample loading station further comprising:

i) a cassette alignment mechanism for aligning said chemical treatment cassette to a predetermined X-Y position;

ii) a sealing gasket sealing said first end of said sampling funnel when said sample funnel is located at said predetermined X-Y position;

iii) a pressure cap having an annular shoulder and center plunger section for press-fit insertion into the mouth of said sample funnel to define a funnel headspace, said shoulder engaging said annular gasket to limit the extent of insertion of said center plunger, said pressure cap having a through-bore gas inlet for introduction of pressurized gas into said funnel headspace to force said sample solution into said inlet port of said mini-column;

c) a chemical treatment station for performing predetermined chemistries on a plurality of preselected retained chemical samples located in said chemical treatment cassette, said chemical treatment station further comprising:

i) a code reader for reading said machine readable code disposed on said chemical treatment cassette to identify the specific chemistry protocols to be performed on said retained chemical samples;

ii) a scanner to identify mini-column addresses wherein said central chamber of said mini-column is populated;

iii) a micro-controller interface for communicating from said code reader to a micro-controller said identified specific chemistry protocols, said micro-controller accessing specific process algorithms pursuant to the specific identified chemistry protocols, said process algorithms defining and communicating to said micro-controller interface stepwise micro-controller control instructions to enable execution of said identified specific chemistries on said preselected chemical samples at said populated mini-column addresses;

iv) a cassette/treatment station interface for enabling near-zero dead volume flow-through communication of said chemical treatment cassette with said chemical treatment station, said cassette/treatment station interface comprising:

a cassette interface dock for precision alignment of said chemical treatment cassette, a first nozzle array comprising a plurality of nozzles spatially arrayed to be congruous with said mini-column inlet ports and reagent well inlet ports for flow-through localized interfacing with said mini-column inlet ports and said reagent well inlet ports, a second nozzle array having a plurality of nozzles spatially arrayed to be congruous with said mini-column outlet ports and reagent well outlet ports for flow through communication with said mini-column outlet ports and said reagent well outlet ports, said first nozzle array positioned above said cassette interface dock, said nozzles in said first array having nozzles tips extending downward towards said cassette interface dock, said second nozzle array position below said cassette interface dock, said nozzles in said second nozzle array having nozzle tips extending upwards to said cassette interface dock, and said nozzles in said first array and said nozzles in said second array establishing said flow-through localized interface by first aligning said chemical treatment cassette in said cassette interface dock and by compression fitting said nozzle tips in said first nozzle array against said tapered opening of said mini-column inlet ports and said reagent well inlet ports, and by compression fitting said nozzle tips in said second nozzle array against said tapered opening of said mini-column outlet ports and said reagent well outlet ports;

v) a chemical delivery subsystem for providing automatic flow through chemistries on said preselected chemical samples further comprising:

a solvent bank providing a plurality of reagents and solvents to said reagent wells for solubilizing said reagents retained therein and for reaction with said chemical samples pursuant to said identified specific chemistry protocols, a rotary valve array further comprising a mini-column inlet port rotary valve array for individual addressing of mini-column inlet ports, a mini-column outlet port rotary valve array for individual addressing of mini-column outlet ports, said mini-column inlet port rotary valve array and said mini-column outlet port rotary valve array being synchronized to a single mini-column address to permit active interface with only one mini-column inlet and outlet port at a time, and a reagent well inlet port rotary valve array for individual addressing of reagent well inlet ports, a reagent well outlet port rotary valve array for individual addressing of reagent well outlet ports, said reagent well inlet port rotary valve array and said reagent well outlet port rotary valve array being synchronized to a single reagent well address to permit active interface with only one reagent well inlet and outlet port at a time, a plurality of accumulators for temporary storage of solvents and reagents, and temporary storage of detached chemical sample to enable chemistries to be performed on said detached samples, and to enable chemistries not including said detached samples to be performed in said mini-column, a mixer/diluter reservoir in communication with said solvent bank, reagent wells, and mini-columns for temporary retention of at least one of a solvent, reagent, sample, and mixtures thereof, a pneumatic pressurizing system for bi-directional transfer of solvents, reagents, and chemical samples to and from said reagent wells, said mini-columns, said accumulators, and said mixer/diluter, and for supplying inert gas to said chemical treatment delivery subsystem, and a valve for integration of an analyzer subsystem into said chemical delivery subsystem to permit automatic analysis of the sample retained in said mini-columns without removal of said mini-columns from said chemical treatment cassette and without disengaging said cassette/treatment station interface.

2. A chemical treatment system as in claim 1 wherein said chemical treatment cassette further comprises an alignment mechanism for aligning said mini-columns such that the longitudinal axis of said mini columns is coincident with the longitudinal axis of said sample funnels.

3. A chemical treatment system as in claim 1 wherein a solid support material is disposed in said central chamber of said mini-column, said solid support material being treated to immobilize said chemical sample, said solid support being retained in said mini-columns by porous frits disposed in said central chamber at said inlet port end and at said outlet port end.

4. A chemical treatment system as in claim 1 wherein said mini-columns are integral to said funnel assembly to provide a unitary, one-piece funnel/mini-column assembly.

5. A chemical treatment system for treatment of less than milligram quantities of a chemical sample, comprising in operative combination:

a) a chemical sample retaining means for holding a plurality of chemical samples for chemical treatment, said chemical sample retaining means further comprising:

i) a sample funneling means for receiving a plurality of chemical sample solutions, said sample funneling means permitting individual addressing of each of said plurality of chemical sampling solutions for chemical treatment;

ii) means for retaining an individual preselected chemical sample, said individual sample retaining means being in flow-through, physical connection with said funneling means, said means permitting near-zero dead volume compression fit with an interface means;

iii) at least one reagent retaining means for retaining preselected reagents, said reagent retaining means permitting flow-through communication there through;

iv) a machine readable code disposed on said chemical sample retaining means for identifying the chemistry protocols to be performed on the retained samples in said individual sample retaining means;

b) a sample loading means for loading sample solutions in said sample funneling means, said sample loading means further comprising:

i) an alignment means for aligning said chemical sample retaining means to a predetermined X-Y position;

ii) a sealing gasket on said sample funneling means on said funneling means;

iii) a pressure cap means for introduction of pressurized gas into said sample funneling means and for forcing a sample solution through said individual sample retaining means;

c) a chemical treatment station for performing predetermined chemistries on a plurality of preselected retained chemical samples located in said chemical sample retaining means, said chemical treatment station further comprising:

i) a code reader for reading said machine readable code disposed on said chemical treatment cassette to identify the specific chemistry protocols to be performed on said retained chemical samples;

ii) a scanner to identify populated mini-column addresses;

iii) a micro-controller interface means for communicating from said code reader to a micro-controller said identified specific chemistry protocols, said micro-controller accessing specific process algorithms pursuant to the specific identified chemistry protocols, said process algorithms defining and communicating to said micro-controller interface step-wise micro-controller control instructions to enable execution of said identified specific chemistries on said pre-selected chemical samples at said populated mini-column addresses;

iv) a chemical cassette/treatment interface means for enabling flow-through localized communication of said chemical sample retaining means with said chemical treatment station, said interface means comprising:

a docking means for precision alignment of said chemical sample retaining means, an interface means for establishing flow-through localized interface between said chemical treatment station and said chemical sample retaining means;

v) a chemical delivery subsystem for providing automatic flow through chemistries on said preselected chemical samples further comprising:

a solvent storage means for providing a plurality of reagents and solvents to said reagent retention means for solubilizing said reagents retained therein and to said chemical sample retaining means for treatment of said chemical samples in said individual sample retaining means pursuant to said identified specific chemistry protocols, a valve means for individual addressing of said individual sample retaining means and for individual addressing of said reagent retention means, a plurality of accumulator means for temporary storage of solvents and reagents, and temporary storage of detached chemical sample to enable chemistries to be performed on said detached samples, and to enable chemistries not including said detached samples as a reactant to be performed in said individual sample retaining means, a mixer/diluter reservoir in communication with said solvent bank, reagent wells, and mini-columns for temporary retention of at least one of a solvent, reagent, sample, and mixtures thereof, a pneumatic pressurizing system for bi-directional transfer of solvents, reagents, and chemical samples to and from said reagent wells, said mini-columns, said accumulators, and said mixer/diluter, and for supplying inert gas to said chemical treatment delivery subsystem, and valve means for integration of an analyzer subsystem into said chemical delivery subsystem to permit automatic analysis of the sample retained in said mini-columns without removal of said mini-columns from said chemical treatment cassette and without disengaging, said cassette/treatment station interface.

6. A chemical treatment system for sequential, uninterrupted treatment of less than milligram quantities of a plurality of chemical samples, comprising in operative combination:

a) a chemical treatment cassette for retaining a plurality of chemical samples for chemical treatment, said chemical treatment cassette further comprising:

i) a funnel assembly comprising a plurality of integrated, individually addressable chemical solution sampling funnels for receiving chemical sample solutions, each of said sampling funnels having a first, open mouth end for introduction of a chemical sample solution, and a tapered, second conical end having a through-hole at the apex of said conical end, said sampling funnels being arranged in an array to permit individual addressing for chemical treatment;

ii) a plurality of sample mini-columns for retaining preselected chemical samples, each of said mini-columns having a centrally disposed chamber extending longitudinally through said mini-column, at least one of said mini-columns having a material selected from at least one of a solid support, dry reagent, dry sample, liquid reagent, liquid sample, and porous frits disposed in said central chamber, said chamber terminating into a first open end, said first open end having a flared, tapered inlet port, said inlet port being in flow-through, physical connection with said through-hole in said conical second end of said funnel, said connection resulting in smooth, continuous transition of the taper from said conical second end of said funnel to said taper of said inlet port, said chamber terminating into a second open end, said second open end having a flared, tapered outlet port, said outlet port being in flow-through communication with said inlet port, said first open end of each of said funnels and said tapered conical second end of each of said funnels and permitting localized access by a compressive fit interface to said mini-column inlet port for near-zero dead volume flow-through communication between said interface and said mini-columns;

iii) at least one reagent well for retaining preselected reagents for reaction with said preselected sample retained in said min-columns, said reagent wells comprising a through-bore parallel to said longitudinal axis of said mini-column, said through-bore terminating in a first end having a flared, tapered inlet port, and terminating in a second end having a flared, outlet port said reagent well inlet port being in flow-through communication with said reagent well outlet port; and iv) a machine readable code disposed on said chemical treatment cassette for identifying the chemistry protocols to be performed on the retained samples in said mini-columns;

b) a sample loading station for loading sample solutions in said sample funnels, said sample loading station including an X-Y positioner for aligning said chemical treatment cassette, and a pressure cap having an annular shoulder and center plunger section for press-fit insertion into the mouth of said sample funnel to define a funnel headspace, said shoulder limiting the extent of insertion of said center plunger, said pressure cap having a though-bore gas inlet for introduction of pressurized gas into said funnel headspace to force said sample solution into said inlet port of said mini-column;

c) a chemical treatment station for performing predetermined chemistries on a plurality of preselected retained chemical samples located in said chemical treatment cassette, said chemical treatment station further comprising:

i) a code reader for reading said machine readable code disposed on said chemical treatment cassette to identify the specific chemistry protocols to be performed on said retained chemical samples;

ii) a scanner to identify mini-column addresses wherein said central chamber of said mini-column is populated;

iii) a micro-controller interface for communicating from said code reader to a micro-controller said identified specific chemistry protocols, said micro-controller accessing specific process algorithms pursuant to the specific identified chemistry protocols, said process algorithms defining and communicating to said micro-controller interface stepwise micro-controller control instructions to enable execution of said identified specific chemistries on said preselected chemical samples at said populated mini-column addresses;

iv) a cassette/treatment station interface for enabling near-zero dead volume flow-through communication of said chemical treatment cassette with said chemical treatment station, said cassette/treatment station interface comprising:
- a cassette interface dock for precision alignment of said chemical treatment cassette,
- a first nozzle array comprising a plurality of nozzles spatially arrayed to be congruous with said mini-column inlet ports and reagent well inlet ports for flow-through localized interfacing with said mini-column inlet ports and said reagent well inlet ports,
- a second nozzle array having a plurality of nozzles spatially arrayed to be congruous with said mini-column outlet ports and reagent well outlet ports for flow through communication with said mini-column outlet ports and said reagent well outlet ports,
- said first nozzle array positioned above said cassette interface dock, said nozzles in said first array having nozzles tips extending downward towards said cassette interface dock,
- said second nozzle array position below said cassette interface dock, said nozzles in said second nozzle array having nozzle tips extending upwards to said cassette interface dock, and
- said nozzles in said first array and said nozzles in said second array establishing said flow-through localized interface by first aligning said chemical treatment cassette in said cassette interface dock and by compression fitting said nozzle tips in said first nozzle array against said tapered opening of said mini-column inlet ports and said reagent well inlet ports, and by compression fitting said nozzle tips in said second nozzle array against said tapered opening of said mini-column outlet ports and said reagent well outlet ports;

v) a chemical delivery subsystem for providing automatic flow through chemistries on said preselected chemical samples further comprising:
- a solvent bank providing a plurality of reagents and solvents to said reagent wells for solubilizing said reagents retained therein and for reaction with said chemical samples pursuant to said identified specific chemistry protocols,
- a rotary valve array further comprising a mini-column inlet port rotary valve array for individual addressing of mini-column inlet ports, a mini-column outlet port rotary valve array for individual addressing of mini-column outlet ports, said mini-column inlet port rotary valve array and said mini-column outlet port rotary valve array being synchronized to a single mini-column address to permit active interface with only one mini-column inlet and outlet port at a time, and a reagent well inlet port rotary valve array for individual addressing of reagent well inlet ports, a reagent well outlet port rotary valve array for individual addressing of reagent well outlet ports, said reagent well inlet port rotary valve array and said reagent well outlet port rotary valve array being synchronized to a single reagent well address to permit active interface with only one reagent well inlet and outlet port at a time,
- a plurality of accumulators for temporary storage of solvents and reagents, and temporary storage of detached chemical sample to enable chemistries to be performed on said detached samples, and to enable chemistries not including said detached samples to be performed in said mini-column,
- a mixer/diluter reservoir in communication with said solvent bank, reagent wells, and mini-columns for temporary retention of at least one of a solvent, reagent, sample, and mixtures thereof,
- a pneumatic pressurizing system for bi-directional transfer of solvents, reagents, and chemical samples to and from said reagent wells, said mini-columns, said accumulators, and said mixer/diluter, and for supplying inert gas to said chemical treatment delivery subsystem, and
- a valve for integration of an analyzer subsystem into said chemical delivery subsystem to permit automatic analysis of the sample retained in said mini-columns without removal of said mini-columns from said chemical treatment cassette and without disengaging said cassette/treatment station interface.

7. A chemical treatment system as in claim 6 wherein said chemical treatment cassette further comprises an alignment mechanism for aligning said mini-columns such that the longitudinal axis of said mini columns is coincident with the longitudinal axis of said sample funnels.

8. A chemical treatment system as in claim 6 wherein a solid support material is disposed in said central chamber of said mini-column, said solid support material being treated to immobilize said chemical sample, said solid support being retained in said mini-columns by porous frits disposed in said central chamber at said inlet port end and at said outlet port end.

9. A chemical treatment system as in claim 6 wherein said mini-columns are integral to said funnel assembly to provide a unitary, one-piece funnel/mini-column assembly.

10. A chemical treatment system for treatment of less than milligram quantities of a chemical sample, comprising in operative combination:
a) a chemical sample retainer for holding a plurality of chemical samples for chemical treatment, said chemical sample retainer further comprising:
  i) a sample funnel for receiving a plurality of chemical sample solutions, said sample funnel permitting individual addressing of each of said plurality of chemical sampling solutions for chemical treatment;
  ii) a retainer for an individual preselected chemical sample, said retainer being in flow-through, physical connection with said funnel, and providing near-zero dead volume compression fit;
  iii) at least one reagent retainer for preselected reagents, said reagent retainer permitting flow-through communication therethrough;
  iv) a machine readable code disposed on said chemical sample retainer for identifying the chemistry protocols to be performed on the retained samples in said individual sample retainer;
b) a sample loading mechanism for loading sample solutions in said sample funnel, and including an X-Y positioner for aligning said chemical sample retainer to a predetermined X-Y position, a sealing gasket, and a pressure cap for introduction of pressurized gas into said sample funnel and for forcing a sample solution through said individual sample retainer;
c) a chemical treatment station for performing predetermined chemistries on a plurality of preselected retained chemical samples located in said chemical sample retainer, said chemical treatment station further including;

i) a code reader for reading said machine readable code disposed on said chemical treatment cassette to identify the specific chemistry protocols to be performed on said retained chemical samples;

ii) a scanner to identify populated mini-column addresses;

iii) a micro-controller interface for communicating from said code reader to a micro-controller said identified specific chemistry protocols, said micro-controller accessing specific process algorithms pursuant to the specific identified chemistry protocols, said process algorithms defining and communicating to said micro-controller interface step-wise micro-controller control instructions to enable execution of said identified specific chemistries on said preselected chemical samples at said populated mini-column addresses;

iv) a chemical cassette/treatment interface for enabling flow-through localized communication of said chemical sample retainer with said chemical treatment station, said interface including a docking mechanism for precision alignment of said chemical sample retainer, and a flow-through localized interface between said chemical treatment station and slid chemical sample retainer;

v) a chemical delivery subsystem for providing automatic flow through chemistries on said preselected chemical samples, the chemical delivery subsystem including solvent storage for a plurality of reagents and solvents to said reagent retainer for solubilizing said reagents retained therein and to said chemical sample retainer for treatment of said chemical samples in said individual sample retainer pursuant to said identified specific chemistry protocols, a valve for individual addressing of said individual sample retainer and for individual addressing of said reagent retainer, a plurality of accumulators for temporary storage of solvents and reagents, and temporary storage of detached chemical sample to enable chemistries to be performed on said detached samples, and to enable chemistries not including said detached samples as a reactant to be performed in said individual sample retainer, a mixer/diluter reservoir in communication with said solvent bank, reagent wells, and mini-columns for temporary retention of at least one of a solvent, reagent, sample, and mixtures thereof, a pneumatic pressurizing system for bi-directional transfer of solvents, reagents, and chemical samples to and from said reagent wells, said mini-columns, said accumulators, and said mixer/diluter, and for supplying inert gas to said chemical treatment delivery subsystem, and a valve integrating of an analyzer subsystem into said chemical delivery subsystem to permit automatic analysis of the sample retained in said mini-columns without removal of said mini-columns from said chemical treatment cassette and without disengaging said cassette/treatment station interface.

* * * * *